(12) United States Patent
Nishida et al.

(10) Patent No.: US 11,066,641 B2
(45) Date of Patent: Jul. 20, 2021

(54) METHOD FOR INDUCING DIFFERENTIATION OF CORNEAL EPITHELIAL CELLS FROM PLURIPOTENT STEM CELLS

(71) Applicant: Osaka University, Suita (JP)

(72) Inventors: Kohji Nishida, Osaka (JP); Ryuhei Hayashi, Osaka (JP); Yuki Ishikawa, Osaka (JP)

(73) Assignee: Osaka University, Osaka (JP)

( * ) Notice: Subject to any disclaimer, the term of this patent is extended or adjusted under 35 U.S.C. 154(b) by 231 days.

(21) Appl. No.: 15/542,200

(22) PCT Filed: Jan. 13, 2016

(86) PCT No.: PCT/JP2016/050784
§ 371 (c)(1),
(2) Date: Jul. 7, 2017

(87) PCT Pub. No.: WO2016/114285
PCT Pub. Date: Jul. 21, 2016

(65) Prior Publication Data
US 2018/0010093 A1 Jan. 11, 2018

(30) Foreign Application Priority Data
Jan. 15, 2015 (JP) .............................. JP2015-006074

(51) Int. Cl.
*C12N 5/079* (2010.01)
*C12N 5/10* (2006.01)
*C12N 5/074* (2010.01)

(52) U.S. Cl.
CPC ......... *C12N 5/0621* (2013.01); *C12N 5/0607* (2013.01); *C12N 5/10* (2013.01); *C12N 2500/90* (2013.01); *C12N 2501/117* (2013.01); *C12N 2501/727* (2013.01); *C12N 2506/45* (2013.01)

(58) Field of Classification Search
CPC ...... C12N 5/0621; C12N 5/10; C12N 5/0607; C12N 2500/90; C12N 2501/117; C12N 2501/727; C12N 2506/45; C12N 2501/16; C12N 2501/155
See application file for complete search history.

(56) References Cited

U.S. PATENT DOCUMENTS

| 6,297,233 | B1 | 10/2001 | Stein et al. |
|---|---|---|---|
| 2007/0155013 | A1 | 7/2007 | Akaike et al. |
| 2007/0280993 | A1 | 12/2007 | Hashimoto et al. |
| 2011/0223140 | A1 | 9/2011 | Park et al. |
| 2012/0142103 | A1 | 6/2012 | Nishida et al. |
| 2012/0283222 | A1 | 11/2012 | Konishi et al. |
| 2014/0094489 | A1 | 4/2014 | Suzuki et al. |
| 2014/0127803 | A1 | 5/2014 | Hayashi et al. |
| 2014/0378459 | A1 | 12/2014 | Fujiyasu et al. |

FOREIGN PATENT DOCUMENTS

| CN | 1929877 | A | 3/2007 | |
|---|---|---|---|---|
| CN | 1934245 | A | 3/2007 | |
| CN | 102712900 | A | 10/2012 | |
| CN | 103184187 | A | 7/2013 | |
| CN | 103492555 | A | 1/2014 | |
| EP | 2700709 | A1 | 2/2014 | |
| JP | 2002-536411 | A | 10/2002 | |
| WO | WO 2009/071601 | A1 | 6/2009 | |
| WO | WO 2010/134619 | A1 | 11/2010 | |
| WO | WO 2010/140698 | A1 | 12/2010 | |
| WO | WO 2011/071048 | A1 | 6/2011 | |
| WO | WO 2012/073238 | A1 | 6/2012 | |
| WO | WO 2012/144582 | A1 | 10/2012 | |
| WO | WO-2012144582 | A1 * | 10/2012 | ........... C12N 5/0621 |
| WO | WO 2012/169579 | A1 | 12/2012 | |
| WO | WO 2013/039187 | A1 | 3/2013 | |
| WO | WO 2013/187533 | A1 | 12/2013 | |

OTHER PUBLICATIONS

Roselló et al. "Mammalian genes induce partially reprogrammed pluripotent stem cells in non-mammalian vertebrate and invertebrate species" eLife. 2013; 2: e00036. (Year: 2013).*
Kim et al. "Technical note: Induction of pluripotent stem cell-like cells from chicken feather follicle cells." J Anim Sci. Aug. 2017;95(8): 3479-3486 (Year: 2017).*
Hu et al. "Memory in induced pluripotent stem cells: reprogrammed human retinal-pigmented epithelial cells show tendency for spontaneous redifferentiation." Stem Cells. Nov. 2010;28(11):1981-91 (Year: 2010).*
Mikhailova et al. "Small-molecule induction promotes corneal epithelial cell differentiation from human induced pluripotent stem cells." Stem Cell Reports. Feb. 6, 2014;2(2):219-31. (Year: 2014).*
Zhang et al. "Differentiation of human embryonic stem cells into corneal epithelial progenitor cells under defined conditions." PLoS One. Aug. 15, 2017;12(8):e0183303. (Year: 2017).*
"Chapter 2: Lens" The Wills Eye Hospital Atlas of Clinical Ophthalmology, 2nd Edition edited by William Tasman and Edward A. Jaeger (Year: 2001).*
Supplementary European Search Report dated Jun. 20, 2018, in EP 16737356.2.
Yu et al. "Differentiation of mouse induced pluripotent stem cells into corneal epithelial-like cells," Cell Biotechnology International, 2013, 37:87-94.
International Search Report dated Mar. 22, 2016, in PCT/JP2015/086070.

(Continued)

*Primary Examiner* — Titilayo Moloye
(74) *Attorney, Agent, or Firm* — Foley & Lardner LLP

(57) ABSTRACT

The present invention relates to a method for inducing the differentiation of corneal epithelial cells from pluripotent stem cells. More specifically, the present invention relates to a method for autonomously differentiating pluripotent stem cells, such as human iPS cells, into ectodermal cell lineage in a serum-free medium without using feeder cells and inducing the differentiation of the resultant ocular surface ectodermal lineage cells into corneal epithelial cells.

2 Claims, 15 Drawing Sheets

(56) References Cited

OTHER PUBLICATIONS

Siddiqui et al., "Two new compounds from the aerial parts of *Bergenia himalaica* Boriss and their anti-hyperglycemic effect in streptozotocin-nicotinamide induced diabetic rats," Journal of Ethnopharmacology, Feb. 15, 2014, 152:561-567.

International Search Report dated Apr. 5, 2016, in PCT/JP2016/050784.

Blalock et al., "Functions of MUC16 in Corneal Epithelial Cells," Investigative Ophthalmology & Visual Science, Oct. 2007, 48(10):4509-4518.

Guenou et al., "Human embryonic stem-cell derivatives for full reconstruction of the pluristratified epidermis: a preclinical study," The Lancet, Nov. 21, 2009, 374:1745-1753.

Hayashi et al., "Co-ordinated ocular development from human iPS cells and recovery of corneal function," Nature, Mar. 17, 2016, 531:376-380.

Hayashi et al., "Generation of Corneal Epithelial Cells from Induced Pluripotent Stem Cells Derived from Human Dermal Fibroblast and Corneal Limbal Epithelium," Plos One, Sep. 2012, 7(9):e45435, 1-10.

Metallo et al., "Retinoic Acid and Bone Morphogenetic Protein Signaling Synergize to Efficiently Direct Epithelial Differentiation of Human Embryonic Stem Cells," Stem Cells, 2008, 26:372-380.

Suga et al., "Self-formation of functional adeno-hypophysis in three-dimensional culture," Nature, Dec. 1, 2011, 480:57-62.

Amit et al., "Feeder Layer and Serum-Free Culture of Human Embryonic Stem Cells," Biology of Reproduction, 2004, vol. 70, pp. 837-845.

Office Action dated May 13, 2019, in Canadian Application No. 2,973,187.

Office Action dated Apr. 23, 2020 in CN 201680006004.8.

* cited by examiner

FIG.13
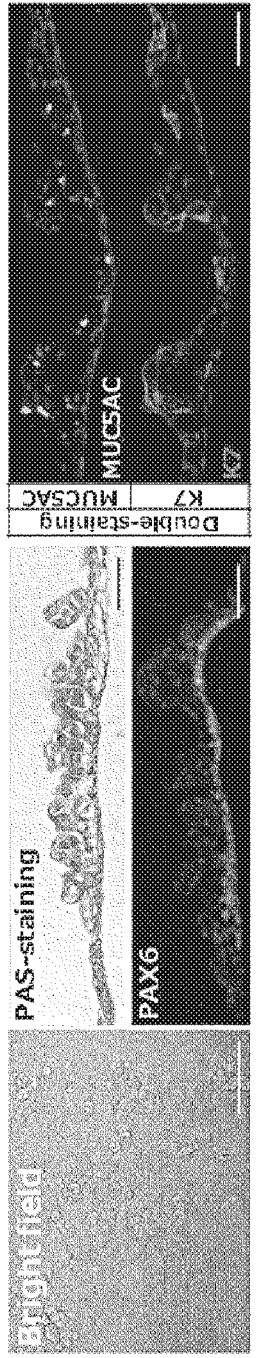
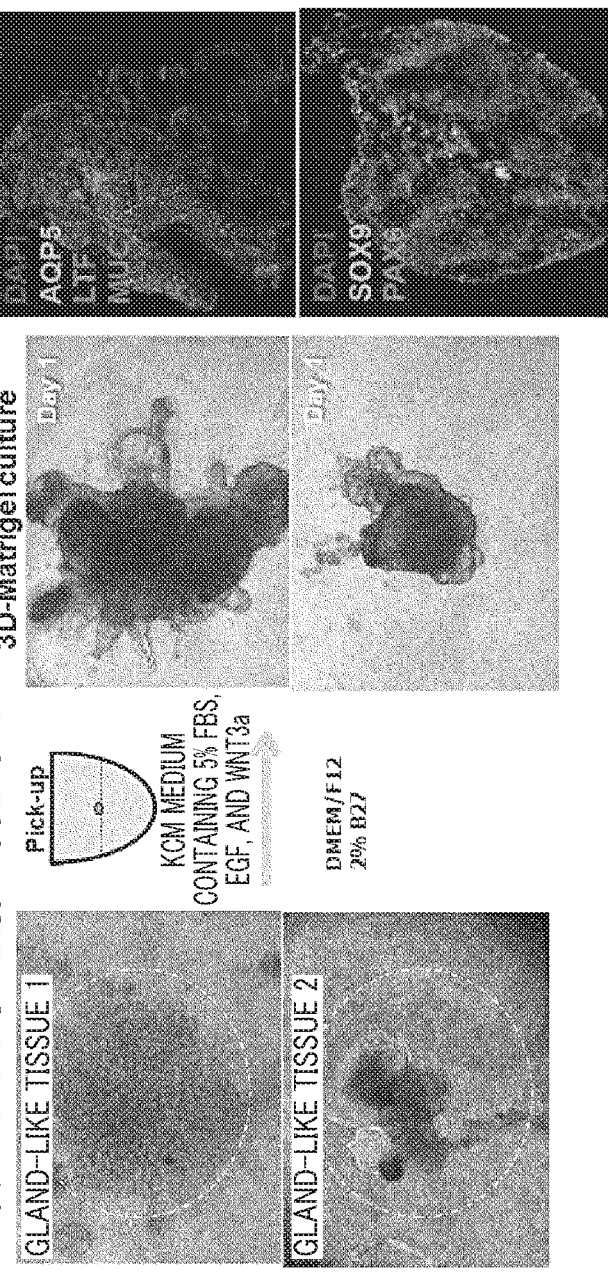

FIG.14
A. DEVELOPMENT OF PERIOCULAR NEURAL CREST CELL
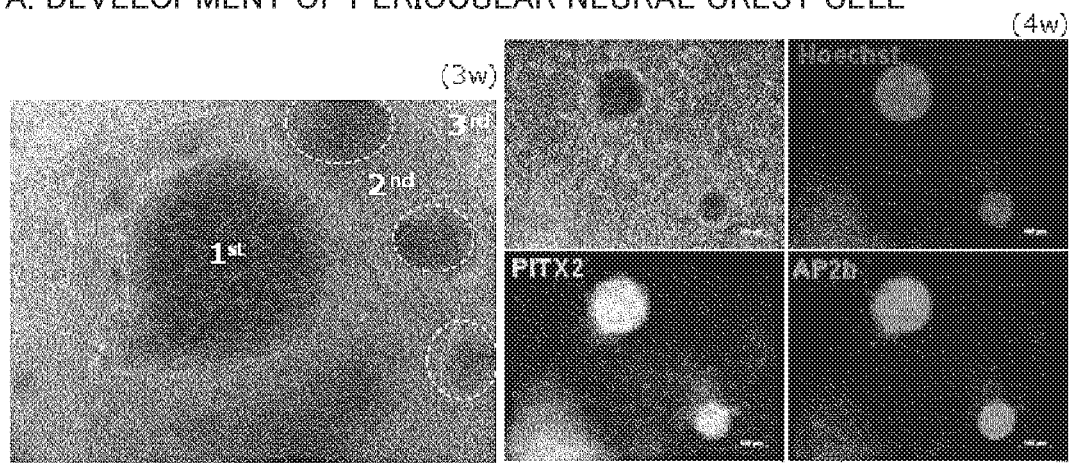
B. EXPRESSION OF PERIOCULAR NEURAL CREST CELL MARKER
[NEURAL CREST MARKER]
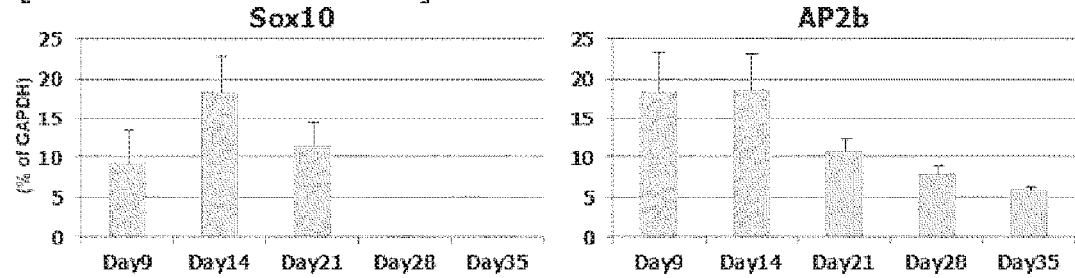
[PERIOCULAR NEURAL CREST MARKER]
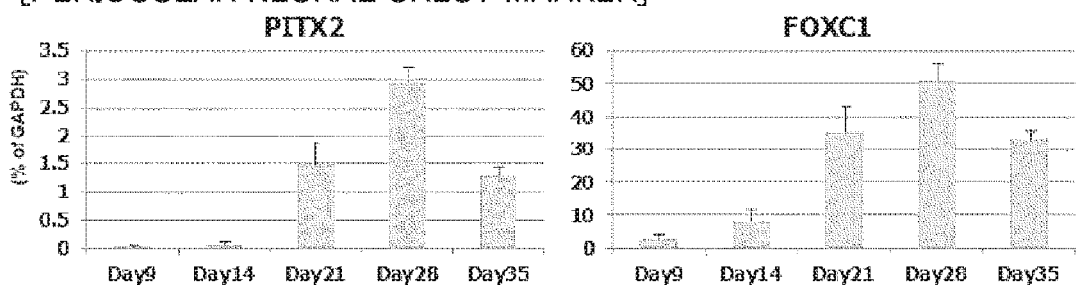

METHOD FOR INDUCING DIFFERENTIATION OF CORNEAL EPITHELIAL CELLS FROM PLURIPOTENT STEM CELLS

RELATED APPLICATIONS

The present application is a National Stage application of PCT/JP2016/050784, filed Jan. 13, 2016, which claims priority to Japanese Patent Application No. 2015-006074, filed on Jan. 15, 2015, the contents of which are incorporated herein by reference.

The present invention relates to a method for inducing the differentiation of corneal epithelial cells from pluripotent stem cells. More specifically, the present invention relates to a method for autonomously differentiating pluripotent stem cells (particularly, induced pluripotent stem cells) into ectodermal cell lineage in a serum-free medium without using feeder cells and inducing the differentiation of the resultant ocular surface ectodermal lineage cells into corneal epithelial cells.

TECHNICAL FIELD

Background Art

In recent years, work has been proceeding on regenerative medicine (cell medicine) for supplementing damaged tissues and organs by inducing the differentiation of undifferentiated cells (stem cells). Particularly, embryonic stem cells (ES cells) can be differentiated into all cells other than placental cells, and thus attention has been given to their differentiation induction into various cell lineage and the identification of a factor determining their differentiation. However, the research and use of the stem cells have many limitations due to the ethical problem of the destruction of fertilized ova in their establishment, and there is also a problem of rejection reaction since ES cells derived from a patient who is to undergo transplantation cannot be established. Thus, in the present situation, diseases to which ES cells are applicable are limited and their clinical usefulness is still not evident.

In contrast, certain factors were introduced into somatic cells or undifferentiated stem cells to establish induced pluripotent stem cells having pluripotent differentiation ability similar to that of ES cells. Typical examples of such induced pluripotent stem cells include iPS cells established by Yamanaka et al. The regenerative medicine using these induced pluripotent stem cells has no ethical problem and also can use patient-derived cells as a source to avoid the problem of rejection reaction.

It has been reported that epithelial cells can be differentiation-induced from human iPS cells or ES cells (Patent Literature 1 and Non Patent Literatures 1 to 2). Many of the induced epithelial cells express stratified epithelial cell markers, such as keratin 14 and p63, also allowing differentiation into stratified epithelial lineage cells, such as cutaneous epithelia. The inventors have reported differentiation into corneal epithelium among stratified epithelia (Patent Literatures 2 to 3 and Non Patent Literature 3); however, the inability to be made into sheet, the inability to induce corneal epithelial progenitor cells having a high growth capacity, and the use of feeder cells have been problems in clinical application.

For clinical application, it is desirable that a corneal epithelium sheet having a stratified, functional tissue structure and the expression of markers (particularly, keratin 12, pax6, and MUC16) can be prepared from human iPS cells without using feeder cells; however, there has heretofore been no such a report.

CITATION LIST

Patent Literature

Patent Literature 1: International Publication No. WO 2012/073238
Patent Literature 2: International Publication No. WO 2010/134619
Patent Literature 3: International Publication No. WO2012/144582

Non Patent Literature

Non Patent Literature 1: Guenou, H., et al., The Lancet 374, (2009) p 1745-1753.
Non Patent Literature 2: Metallo, C. M., et al., Stem cells (2008) 26, 372-380.
Non Patent Literature 3: R. Hayashi et al., Volume 7, Issue 9, e45435, PLOS ONE, 2012

SUMMARY OF INVENTION

Technical Problem

An object of the present invention is to provide a method for inducing the differentiation of pluripotent stem cells (particularly, induced pluripotent stem cells) into an ocular surface epithelial lineage, such as corneal epithelium or conjunctival epithelium, without using feeder cells or serum and to provide a stratified, functional cultured corneal epithelial cell sheet from pluripotent stem cells (particularly, induced pluripotent stem cells).

Solution to Problem

The present inventors have conducted intensive studies for solving the above problems, and have found that when human iPS cells are cultured in a differentiation medium containing KSR and the like without using serum or feeder cells, the cells autonomously differentiate in about 4 weeks and form a (multi-zone) colony consisting of concentric zones of different ectodermal cell lineage. In addition, it has been found that ocular surface ectodermal lineage cells including epithelial stem cells can be separated from the resultant colony, and that corneal epithelial progenitor cells are differentiation-induced, isolated and further maturation-cultured to provide stratified corneal epithelial cells. The resultant corneal epithelial cells can be recovered in sheet form and transplanted and have been confirmed to function as corneal epithelium in vitro and in vivo like corneal epithelial cells derived from somatic cells.

The present invention has been accomplished based on the above findings, and relates to the following (1) to (15):

(1) A method for producing a colony consisting of concentric zones of different ectodermal cell lineage, comprising subjecting pluripotent stem cells (particularly, induced pluripotent stem cells) to two-dimensional culture in a serum-free medium without using feeder cells;

(2) The method according to (1) above, wherein the concentric zones of different ectodermal cell lineage are formed by autonomous differentiation of the pluripotent stem cells;

(3) The method according to (1) or (2) above, wherein the serum-free medium does not contain 0.5 nM or more of BMP4 (bone morphogenetic protein 4), transforming growth factor, or activin;

(4) The method according to (3) above, wherein the serum-free medium further does not contain at least one selected from the group consisting of high concentration retinoic acid, a BMP inhibitor, a TGFβ inhibitor, and Noggin;

(5) The method according to any one of (1) to (4) above, wherein the pluripotent stem cells are cultured using a vessel coated with one or more selected from the group consisting of collagen, fibronectin, laminin or laminin fragments, vitronectin, basement membrane matrices, gelatin, hyaluronic acid, polylysine, vitronectin, and hyaluronic acid;

(6) The method according to any one of (1) to (5) above, wherein the colony comprises zones of neuroectodermal lineage cells, neural crest lineage cells/optic cup lineage cells, ocular surface ectodermal lineage cells, and surface ectodermal lineage cells, respectively;

(7) A method for producing eye-related cells, comprising the steps of:
producing a colony consisting of concentric zones of different ectodermal cell lineage by the method according to any one of (1) to (6) above,
separating cells contained in a particular zone from the colony, and
inducing the differentiation of the cells into eye-related cells;

(8) The method according to (7) above, wherein the eye-related cells are any one selected from the group consisting of corneal epithelial cells, retinal pigment epithelial cells, neuroretinal cells, conjunctival epithelial cells, limbal epithelial cells, corneal endothelial cells, keratocytes, iris stromal cells, scleral cells, iris pigment epithelial cells, ciliary epithelial cells, optic nerve cells, sublimbal fibroblasts, subconjunctival fibroblasts, lacrimal gland cells, meibomian gland cells, goblet cells, lens epithelial cells, and eyelid epithelial cells;

(9) A method for producing corneal epithelial cells, comprising the steps of:
producing a colony consisting of concentric zones of different ectodermal cell lineage by the method according to any one of (1) to (6) above,
culturing the colony in a medium containing a growth factor,
separating cells contained in a zone of ocular surface ectodermal lineage cells and culturing the cells in a medium containing KGF, a Rock inhibitor, and a serum substitute to induce differentiation into corneal epithelial progenitor cells, and
isolating the corneal epithelial progenitor cells and inducing differentiation into corneal epithelial cells;

(10) The method according to (9) above, wherein the corneal epithelial cells are isolated using the presence or absence of expression of one or more markers selected from the group consisting of ITGβ4, SSEA4, TRA-1-60, and CD200, preferably ITGβ4 positivity and SSEA4 positivity, more preferably TRA-1-60 or CD200 negativity and ITGβ4 positivity and SSEA4 positivity, still more preferably CD200 negativity and ITGβ4 positivity and SSEA4 positivity, as an index;

(11) Corneal epithelial cells produced by the method according to (9) or (10) above, the corneal epithelial cells being K12-, pax6-, and p63-positive;

(12) A method for producing a corneal cell sheet, comprising a step of producing corneal epithelial cells by the method according to (9) or (10) above and a step of further subjecting the resultant corneal epithelial cells to stratification culture;

(13) A colony consisting of concentric zones of different ectodermal cell lineage derived from pluripotent stem cells (particularly, induced pluripotent stem cells);

(14) The colony according to (13) above, produced by the method according to any one of (1) to (6) above;

(15) A stratified corneal epithelial cell sheet derived from pluripotent stem cells (particularly, induced pluripotent stem cells), wherein the corneal epithelial cells are K12-, pax6-, and MUC16-positive; and

(16) Corneal epithelial cells derived from pluripotent stem cells (particularly, induced pluripotent stem cells) produced by separating and culturing cells contained in a zone of ocular surface ectodermal lineage cells in the colony according to (13) or (14), the corneal epithelial cells being K12-, pax6-, and p63-positive.

Advantageous Effects of Invention

A method has heretofore been reported for inducing epithelial cells from human iPS cells; however, stratified functional cells have not been prepared which hold markers specific for corneal epithelial cells, such as keratin 12, pax6, and MUC16. The epithelial cells obtained by the method of the present invention express these markers, are transplantable, and function as corneal epithelial cells in vitro and in vivo like corneal epithelial cells derived from somatic cells. The method of the present invention does not use animal-derived feeder cells or serum; thus, the cells obtained are highly safe and suited for clinical application.

In addition, not only corneal epithelial cells but also various cells constituting the eye, such as conjunctival epithelial cells, retinal cells, and lacrimal gland cells, can be prepared from the colony consisting of concentric zones of different ectodermal cell lineage obtained by the method of the present invention.

BRIEF DESCRIPTION OF DRAWINGS

FIG. 2 is a series of photographs showing a process of inducing differentiation from human iPS cells to ocular surface epithelial/corneal epithelial cells in which FIG. 2A is a series of photographs at day 0, day 5, day 10, day 15, day 20, and day 25, and FIG. 2B is a photograph at 6 weeks after.

FIG. 3 is a series of photographs showing features of cells contained in zones of ectodermal cells autonomously differentiated from human iPS cells in which FIG. 3A shows the expression of pax6 and p63 in the 1st to 3rd zones, FIG. 3B, the expression of pax6 and p63 in the 2nd to 4th zones, FIG. 3C, the expression of E-cadherin and p63 in the 1st to 3rd zones, and FIG. 3D, the expression of βIII-tublin and p63 in the 1st to 3rd zones. These results show the presence of p63/pax6 double positive ocular surface epithelial cells only in the 3rd zone.

FIG. 4A shows the appearance of CHX10-positive neuroretinal cells in the inner of the 2nd zone and retinal pigment epithelial cells in the outer; FIG. 4B shows the appearance of p75/SOX10 double positive neural crest cells in the presumptive region of the 2nd zone at about the 2nd week of differentiation; and FIG. 4C shows the appearance of lens cells in the 2nd to 3rd zones at the 4th week of differentiation and their wide dispersion in the 2nd to 3rd zone portions through a differentiation induction process.

FIG. 7 is a series of photographs showing the expression of corneal epithelium-related markers during mouse eye development (E9.5 to 18.5) (PCE: a presumptive region of corneal epithelium, OSEpi: ocular surface epithelium, CE: corneal epithelium, CS: corneal stroma, LV: lens vesicle, LE: lens, AC: anterior chamber, EL: eyelid, and OV: ocular vesicle).

FIG. 10 is a series of photographs showing the results of observing characteristics of corneal epithelial cells differentiated from human iPS cells using marker expression. Corneal epithelial cells are observed in the 3rd zone (P3) and conjunctival epithelium and other pax6-negative stratified epithelial cells are observed in the 2nd zone (P2).

FIG. 11A shows that corneal epithelial cells derived from human iPS cells have a cobblestone-like form and are stratified into 3 to 4 zones. FIG. 11B shows that cells after maturation culture express markers, ZO-1, MUC1, MUC4, and MUC16, essential for corneal barrier function. FIG. 11C shows that as a result of FACS analysis of human iPS cell-derived corneal epithelial cells for K14 and K12, about 99% of the cells were K14-positive and that about 60% were K12-positive.

FIG. 13 is a series of photographs showing conjunctival goblet cell-like cells and lacrimal gland-like cells appearing during long-term culture in a medium for corneal epithelium culture. FIG. 13A shows that the PAS-positive and PAX6-positive cell population expresses MUC5AC and K7 as markers of conjunctival goblet cells. FIG. 13B shows that the gland tissue obtained by subjecting a cell aggregate having a gland-like structure to three-dimensional culture in Matrigel expresses AQP5, LTF, and MUC7 as markers of the lacrimal gland/salivary gland.

FIG. 14 illustrates the induction of periocular neural crest cells. FIG. 14A shows that the cell mass induced from a multi-zone structure expresses PITX2 and AP2b as markers of periocular neural crest cells. FIG. 14B shows that as a result of RT-PCR, SOX10 as an initial neural crest marker disappeared in 4 weeks, and then the expression of markers of the periocular neural crest, such as PITX2 and FOXC1, was induced.

DESCRIPTION OF EMBODIMENTS

1. Definition

Figure 1:
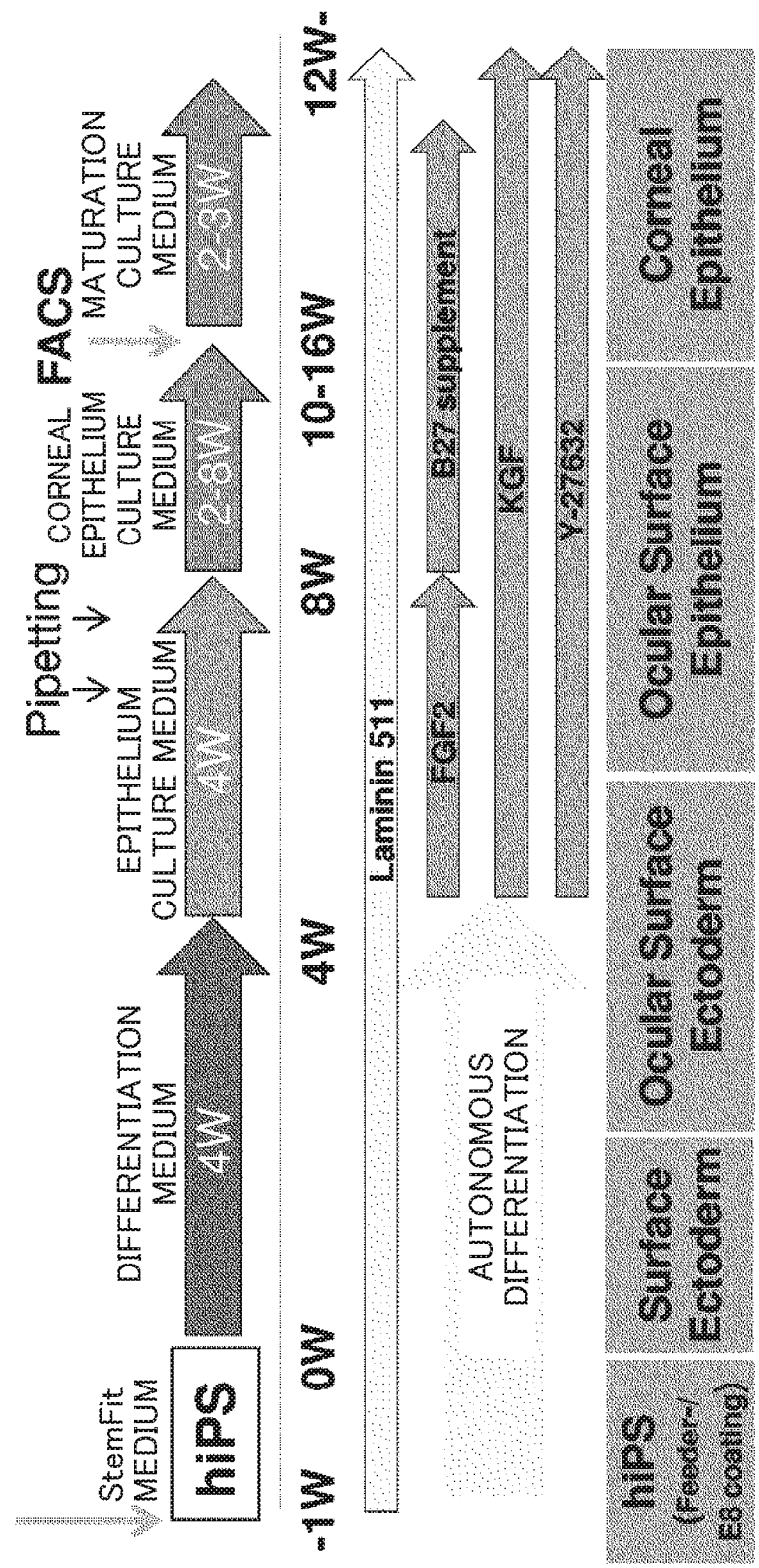
FIG. 1 is a diagram showing a scheme of a method for inducing differentiation from human iPS cells to ocular surface epithelial/corneal epithelial cells.

Some of the terms used herein will be described below.
(1) Pluripotent Stem Cell The term "pluripotent stem cell" used herein includes all cells with pluripotent differentiation activity that are capable of differentiating into all cells other than placental cells, and also encompasses an ES cell and an ES cell line as well as induced pluripotent stem cells, such as an iPS cell.

The term "induced pluripotent stem cell" refers to a cell reprogrammed (initialized) to have pluripotent differentiation activity similar to that of an ES cell by introducing certain factors into a mammal somatic cell or undifferentiated stem cell.

The "induced pluripotent stem cell" was first established by Yamanaka et al. by introducing the 4 factors of Oct3/4, Sox2, Klf4, and c-Myc into a mouse fibroblast, and designated "iPS cell (induced pluripotent stem cell)" (Takahashi K, Yamanaka S., Cell, (2006) 126: 663-676). Thereafter, a human iPS cell was also established by introducing the same 4 factors into a human fibroblast (Takahashi K, Yamanaka S., et al. Cell, (2007) 131: 861-872.; Okita, K., Ichisaka, T., and Yamanaka, S. (2007). Nature 448, 313-317.), and methods for establishing a safer iPS cell less inducing tumor formation, such as a method that does not use c-Myc, (Nakagawa M, Yamanaka S., et al. Nature Biotechnology, (2008) 26, 101-106) were further successfully established.

Thomson et al. of the University of Wisconsin succeeded in establishing an induced pluripotent stem cell prepared by introducing the 4 genes of Oct3/4, Sox2, NANOG, and LIN28 (Yu J., Thomson J A. et al., Science (2007) 318: 1917-1920.). Daley et al. of Harvard University also reported the establishment of an induced pluripotent stem cell prepared by introducing the 6 genes of Oct3/4, Sox2, KLF4, C-MYC, hTERT, and SV40 large T into a cutaneous cell (Park I H, Daley G Q. et al., Nature (2007) 451: 141-146).

Sakurada et al. reported a more efficiently induced pluripotent stem cell obtained by introducing Oct3/4, Sox2, Klf4, and c-Myc, and the like using an undifferentiated stem cell present in tissue after birth but not a somatic cell as a cell source (Japanese Patent Laid-Open No. 2008-307007).

In addition, there were reported an induced pluripotent stem cell prepared by introducing Oct3/4, KLF4, and a low-molecular compound into a mouse neural progenitor cell or the like (Shi Y., Ding S., et al., Cell Stem Cell, (2008) Vol 3, Issue 5, 568-574), an induced pluripotent stem cell prepared by introducing Oct3/4 and KLF4 into a mouse neural stem cell endogenously expressing Sox2 and C-MYC (Kim J B., Scholer H R., et al., Nature, (2008) 454, 646-

650), and an induced pluripotent stem cell prepared using a Dnmt inhibitor or an HDAC inhibitor without using C-MYC (Huangfu D., Melton, D A., et al., Nature Biotechnology, (2008) 26, No 7, 795-797).

Examples of known patent literatures including the above relating to an induced pluripotent stem cell include Japanese Patent Laid-Open Nos. 2008-307007 and 2008-283972, U.S. Patent Nos. 2008-2336610 and 2009-047263, and International Publication Nos. WO 2007-069666, WO 2008-118220, WO 2008-124133, WO 2008-151058, WO 2009-006930, WO 2009-006997, and WO 2009-007852.

The term "induced pluripotent stem cell" used herein includes known induced pluripotent stem cells and all induced pluripotent stem cells equivalent thereto provided that it satisfies the definition described at the outset and does not impair the effects of the present invention, and the cell source, the introduced factors, the introduction method, and the like are not particularly limited.

The cell source is preferably derived from a human (a human induced pluripotent stem cell), more preferably derived from a patient per se in need of treatment using an epithelial progenitor cell/stem cell population, an epithelial cell population including a corneal epithelial cell, or an epidermal cell population which has been differentiated from the stem cell.

(2) Ectodermal Cell Lineage

The human embryo generates three germ lines, i.e. endoderm, mesoderm, and ectoderm, during the stage of development. That is, it generates endoderm, mesoderm, and ectoderm. Among these, the mesoderm becomes the mucosal epithelium of stomach and small bowel, liver, pancreas, or the like; the mesoderm becomes muscle, bone, blood vessel, blood, subcutaneous tissue, heart, kidney, or the like; and the ectoderm forms nerve, eyes, epiderm, or the like. The term "ectodermal cell lineage" used herein means cell lineage derived from the ectoderm, i.e. cells forming the central nervous system/sensory organs, epiderm, or eyes in the future.

Examples of the "ectodermal cell lineage cell" include neuroectodermal lineage cells, neural crest lineage cells/optic cup lineage cells, ocular surface ectodermal lineage cells, and surface ectodermal lineage cells.

The "neuroectodermal lineage cell" is a cell capable of differentiating into nerve-related cells in the future, and is characterized as a Sox2+, TUBB3+, Sox6+ cell.

The "neural crest lineage cell" is a cell capable of differentiating into neural crest-related cells, such as a peripheral nerve cell, a glia cell, a pigment cell, a corneal endothelial cell, and a keratocyte, and is characterized as a sox10-positive, pax6-negative cell.

The "optic cup lineage cell" is a cell capable of differentiating into optic cup-related cells, such as retina, retinal pigment epithelium, and iris pigment epithelium, and is characterized as an Rx+ cell.

The "ocular surface ectodermal lineage cell" is a cell capable of differentiating into ocular surface cells, such as corneal epithelium and conjunctival epithelium, and is characterized as a pax6+, p63+, E-cadherin+ cell.

(3) Eye-Related Cell

The "eye-related cell" used herein means a cell forming an eye derived from ectoderm, and examples thereof include a corneal epithelial cell, a retinal pigment epithelial cell, a neuroretinal cell, a conjunctival epithelial cell, a limbal epithelial cell, a corneal endothelial cell, a keratocyte, an iris stromal cell, a scleral cell, an iris pigment epithelial cell, a ciliary epithelial cell, an optic nerve cell, a sublimbal fibroblast, a subconjunctival fibroblast, lacrimal gland, meibomian gland, a goblet cell, a lens epithelial cell, and an eyelid epithelial cell.

(4) Corneal Epithelial Cell and Corneal Epithelial Progenitor Cell

Cornea has the 3-layered structure of a corneal epithelial layer, a corneal stromal layer, and a corneal endothelial layer in order from the surface. "Corneal epithelial cells" are cells constituting the outermost layer of cornea and consist of 4 to 5 corneal epithelial cell layers. The "corneal epithelial cell" is derived from the epidermal ectoderm while the corneal stroma and endothelium are derived from the neural crest; there are considered to be separate stem cells therefor. In the present invention, the "corneal epithelial cell" is characterized by the expression of keratin 12 as a corneal epithelial differentiation marker in addition to pax6 and p63.

The "corneal epithelial progenitor cell" is an undifferentiated corneal epithelial cell, characterized by the expression of pax6 and p63, and little expresses keratin 12 (K12) as a differentiation marker.

(5) Cell Marker

In the present invention, a marker specific for each cell lineage is used to identify a differentiated cell. Typical markers will be described below.

Keratin 14 (cytokeratin 14: K14): keratin 14 is a typical marker of a basal epithelial cell.

p63: p63, which is a nuclear protein belonging to the p53 gene family, is a typical marker of an epithelial progenitor cell/stem cell and is observed to be expressed in normal human epidermal and follicular basal cells.

Keratin 12 (cytokeratin 12: K12): keratin 12 and 3 are typical specific differentiation markers of the corneal epithelium.

Pax6 (paired homeobox-6): pax6 is a transcriptional regulatory factor, is involved in eye formation, and is a typical marker for corneal epithelial, lens epithelial, and retinal cells.

MUC16 (mucin 16): MUC16 is a type of membrane-bound mucin, is selectively expressed in a corneal epithelial cell, and has important roles in the maintenance of the mucin layer on the ocular surface and the exertion of barrier function.

2. Autonomous Differentiation of Pluripotent Stem Cell

According to the present invention, pluripotent stem cells are first autonomously differentiated to form a colony consisting of concentric zones of different ectodermal cell lineage. The term "autonomous differentiation (autonomously differentiating)" means that a cell differentiates on its account without receiving an external stimulus, such as a differentiation inducer or a differentiation induction promoter.

(1) Medium

According to the present invention, culture is carried out using a serum-free medium. The term "serum-free medium" means an unconditioned or unpurified serum-free medium, and a medium contaminated by purified blood-derived components or animal tissue-derived components (e.g., growth factor) corresponds to the serum-free medium.

As a basal medium for differentiation, any of media usable for animal cell culture, such as DMEM medium, BME medium, αMEM medium, serum-free DMEM/F12 medium, BGJb medium, CMRL 1066 medium, Glasgow MEM medium, Improved MEM Zinc Option medium, IMDM medium, Medium 199 medium, Eagle MEM medium, Ham's medium, RPMI 1640 medium, Fischer's medium, McCoy's medium, and Williams E medium, may be used; however, media for stem cells, such as KnockOut™ DMEM, Medium 154, and StemPro® hESC SFM, are preferable.

As a basal medium for maintenance, a medium for pluripotent stem cells, free of animal/human-derived components is more preferable, and as such a medium, commercial media, such as mTeSR™ 1 (BD Japan Co., Ltd.) and StemFit® may also be used.

The medium may contain "serum substitute". Examples of the serum substitute include albumin (e.g., lipid-rich albumin), transferrin, fatty acids, collagen precursors, trace elements (e.g., zinc and selenium), B-27® supplement, N2 supplement, knock-out serum replacement (KSR from Invitrogen Co., Ltd.), 2-mercaptoethanol, and 3' thiol glycerol. The concentration thereof in the medium is 0.01 to 10% by weight, preferably 0.5 to 4% by weight for B-27 supplement.

Various nutrient sources necessary for the maintenance and growth of cells and components necessary for differentiation induction may be properly added to the medium. For example, as the nutrient sources, the medium may contain: carbon sources, such as glycerol, glucose, fructose, sucrose, lactose, honey, starch, and dextrin; carbohydrates, such as fatty acid, oil and fat, lecithin, and alcohol; nitrogen sources, such as ammonium sulfate, ammonium nitrate, ammonium chloride, urea, and sodium nitrate; inorganic salts, such as common salt, potassium salt, phosphate, magnesium salt, calcium salt, iron salt, and manganese salt; monopotassium phosphate, dipotassium phosphate, magnesium sulfate, sodium chloride, ferrous sulfate, sodium molybdate, sodium tungstate, and manganese sulfate; vitamins; and amino acids.

According to the present invention, the pluripotent stem cell autonomously differentiates into an ectodermal cell lineage and thus the medium is not required to contain a differentiation inducer, such as BMP4 (bone morphogenetic protein 4), transforming growth factor, or activin. Specifically, the medium does not substantially contain one or more, preferably two or more, more preferably all of the differentiation inducers. BMP4 may be contained at a concentration of on the order of less than 0.5 nM, but is preferably not contained at all.

The medium is also not required to contain a differentiation induction promoter, such as high concentration retinoic acid, a BMP inhibitor, a TGFβ inhibitor, or Noggin. The high concentration retinoic acid means on the order of 1 µM, particularly 10 µM of retinoic acid. In other words, the medium does not contain one or more, preferably two or more, more preferably all of the differentiation induction promoters. In addition, the medium is also not required to contain Wnt, a Wnt signal activator, chordin, or the like.

The medium obtained by blending the above components has a pH of 5.5 to 9.0, preferably 6.0 to 8.0, more preferably 6.5 to 7.5.

(2) Culture Condition

According to the present invention, pluripotent stem cells are subjected to two-dimensional culture without using feeder cells. The vessel is not particularly limited provided that it is used for cell culture; a flask, a flask for tissue culture, a dish, a petri dish, a dish for tissue culture, a multi dish, a microplate, a microwell plate, a multi plate, a multi well plate, a microslide, a chamber slide, a schale, a tube, a tray, a culture bag, and a roller bottle can be used.

To promote the adhesion and spreading of cells, the inner surface of the vessel is preferably coated with any one or more selected from the group consisting of collagen, fibronectin, laminin or laminin fragments, vitronectin, basement membrane matrices, gelatin, hyaluronic acid, polylysine, vitronectin, and hyaluronic acid. Among others, laminin or laminin fragments, such as laminin E8 fragment and laminin 511E8 fragment, are preferably used.

Culture is carried out under conditions of 36° C. to 38° C., preferably 36.5° C. to 37.5° C., 1% to 25% $O_2$, and 1% to 15% $CO_2$.

The culture period for autonomous differentiation is at longest 1 week to 8 weeks, preferably 2 weeks to 6 weeks, more preferably 3 weeks to 5 weeks.

(3) Colony Formation

The pluripotent stem cells subjected to two-dimensional culture without using feeder cells in a serum-free medium autonomously differentiate to form a multi-zone colony of ectodermal cell lineage. The colony consists of concentric zones of different ectodermal cell lineage from the center to the periphery, and comprises a 1st zone (neuroectodermal lineage cells (Sox2+, TUBB3+, Sox6+)), a 2nd zone (neural crest lineage cells/optic cup lineage cells (pax6+, Sox10+, Rx+)), a 3rd zone (ocular surface ectodermal lineage cells (pax6+, p63+, E-cadherin+)), and a 4th zone (surface ectodermal lineage cells (p63+, E-cadherin+)).

3. Induction of Differentiation of Eye-Related Cell From Colony

The colony formed by the autonomous differentiation of pluripotent stem cells consists of concentric zones of different ectodermal cell lineage, which comprises distinct zones of cell populations; the 1st zone (neuroectodermal lineage cells), the 2nd zone (neural crest lineage cells/optic cup lineage cells), the 3rd zone (ocular surface ectodermal lineage cells), and the 4th zone (surface ectodermal lineage cells). The cell lineage contained in each zone of the colony is in a different lineage; thus, using this, a cell contained in a particular zone can be separated (isolated) and differentiated to provide an intended eye-related cell.

Thus, the present invention provides a method for producing an eye-related cell, which comprises producing a colony consisting of concentric zones of different ectodermal cell lineage by the method described in the above paragraph, separating a cell contained in a particular zone from the colony, and inducing the differentiation of the cell into an eye-related cell.

For example, the conjunctival epithelial cell is differentiated from the ocular surface epithelial cell lineage consisting of the 3rd zone cells like the corneal epithelium. After culture in a corneal epithelium differentiation medium, FACS can be used to isolate a conjunctival epithelial cell as a pax6-positive, K13-positive, K12-negative cell from among cells isolated as SSEA4-negative, ITGB4-positive cells.

The retinal pigment epithelial cells are cells derived from the neuroectoderm, and thus can be observed as cobblestone-like epithelial cells with pigment in the 1st to 2nd zone during differentiation induction. The pigment cells can be visually isolated under a microscope, and the picked-up pigment epithelial colony can be subjected to isolation culture, in a medium, such as DMEM containing 10% FBS, for example, on a culture dish coated with gelatin.

The neural crest cell appears in the 2nd zone at the early stage (about 2 weeks) of differentiation induction, and thus it is possible to recover the cell at or after 2 weeks and isolate the cell by FACS using a neural crest cell marker, such as p75NTR or ITGA4. The neural crest cell obtained can be differentiated into a corneal epithelial cell. The initial neural crest cell is induced into a periocular neural crest cell by continuing culture. The periocular neural crest cell can be identified through the expression of a periocular neural crest marker, such as PITX2 or FOXC1.

4. Induction of Differentiation of Corneal Epithelial Cell From Pluripotent Stem Cell The epithelial progenitor cell capable of differentiating into the corneal epithelium is present in the 2nd and 3rd zones of the colony, and particularly the corneal epithelial progenitor cell is present in the 3rd zone (ocular surface ectodermal lineage cells). Thus, the ocular surface ectodermal lineage cells can be differentiated into corneal epithelial progenitor cells, which are then isolated and subjected to maturation culture to provide corneal epithelial cells.

Specifically, a colony having the form of concentric circles is formed by autonomous differentiation from pluripotent stem cells and then cultured by replacement with a differentiation medium for epithelium, containing a growth factor. This results in the appearance of ocular surface epithelial stem cells characterized by pax6+, p63+, and E-cadherin+ in the 3rd zone.

The ocular surface epithelial stem cells are separated by pipetting or the like, cultured in a medium for corneal epithelium culture, and differentiated into corneal epithelial progenitor cells. Then, the corneal epithelial progenitor cells are isolated using FACS or the like and subjected to maturation culture to provide corneal epithelial cells.

In each step of differentiation induction, culture is carried out in a serum-free medium without using feeder cells. The medium and culture conditions will be described below.

(1) Medium (1-1) Differentiation Medium for Epithelium

To promote differentiation into an epithelial stem cell, the differentiation medium for epithelium contains growth factors, such as KGF, a Rock inhibitor, bFGF, and a serum substitute. The basal medium to be used may be any medium, such as DMEM medium, BME medium, or αMEM medium, which are used for autonomous differentiation, provided that it is a medium (serum-free medium) usable for the culture of an epithelial cell. A medium for stem cells, such as KnockOut™ DMEM, Medium 154, or StemPro® hESC SFM, an epithelial cell culture medium, such as CNT20, Cnt50, CnT-PR, or KSFM, or their mixed medium is desirable. In Examples to be described later, 50% of a serum-free medium for autonomous differentiation and 50% of Cnt20 or CntPR were mixed for use.

(1-2) Medium for Corneal Epithelium Culture

To promote the induction of differentiation into a corneal epithelial progenitor cell, the medium for corneal epithelium culture can contain KGF, a Rock inhibitor, and a serum substitute (e.g., B27-supplement). In addition, it may contain FGF2, insulin, and transferrin. The "Rock inhibitor" means a substance inhibiting Rho kinase (ROCK: Rho-associated, coiled-coil containing protein kinase); for example, N-(4-pyridinyl)-4β-[(R)-1-aminoethyl]cyclohexane-1α-carboxamide (Y-27632), Fasudil (HA1077), (2S)-2-methyl-1-[(4-methyl-5-isoquinolinyl)sulfonyl]hexahydro-1H-1,4-diazepine (H-1152), 4β-[(1R)-1-aminoethyl]-N-(4-pyridyl)benzene-1α-carboxamide (Wf-536), N-(1H-pyrrolo[2,3-b]pyridin-4-yl)-4PER(R)-1-aminoethyl] cyclohexane-1α-carboxamide (Y-30141), N-(3-{[2-(4-amino-1,2,5-oxadiazol-3-yl)-1-ethyl-1H-imidazo[4,5-c] pyridin-6-yl]oxy}phenyl)-4-{[2-(4-morphorinyl)ethyl]-oxy}benzamide (GSK269962A), and N-(6-fluoro-1H-indazol-5-yl)-6-methyl-2-oxo-4-[4-(trifluoromethyl)phenyl]-3,4-dihydro-1H-pyridine-5-carboxamide (GSK429286A) can be used.

As the basal medium, the same medium as the differentiation medium for epithelium can be used.

(1-3) Medium for Maturation Culture

Although the corneal epithelium can be stratified and maturated using the above corneal epithelium medium, culture using a serum-containing medium for maturation culture for about the last 1 week promotes stratification and maturation. The medium for maturation culture preferably contains serum (if necessary), KGF, a Rock inhibitor, insulin, transferrin, and selenium. As the basal medium, the same medium as the medium for corneal epithelium culture can be used.

All media (the differentiation medium for epithelium, the medium for corneal epithelium culture, and the medium for maturation culture) may contain "serum substitute". Examples of the serum substitute include those described in the above paragraph, for example, albumin (e.g., lipid-rich albumin), transferrin, fatty acids, collagen precursors, trace elements (e.g., zinc and selenium), B-27® supplement, and N2 supplement. The concentration thereof in the medium is 0.01 to 10% by weight, preferably 0.5 to 4% by weight for the B-27 supplement.

Various nutrient sources necessary for the maintenance and growth of cells and components necessary for differentiation induction may be properly added to the medium. For example, as the nutrient sources, the medium may contain: carbon sources, such as glycerol, glucose, fructose, sucrose, lactose, honey, starch, and dextrin; carbohydrates, such as fatty acid, oil and fat, lecithin, and alcohol; nitrogen sources, such as ammonium sulfate, ammonium nitrate, ammonium chloride, urea, and sodium nitrate; inorganic salts, such as common salt, potassium salt, phosphate, magnesium salt, calcium salt, iron salt, and manganese salt; monopotassium phosphate, dipotassium phosphate, magnesium sulfate, sodium chloride, ferrous sulfate, sodium molybdate, sodium tungstate, and manganese sulfate; vitamins; and amino acids.

(2) Culture Condition

In each step, culture is carried out without using feeder cells. The vessel is not particularly limited provided that it is used for cell culture; a flask, a flask for tissue culture, a dish, a petri dish, a dish for tissue culture, a multi dish, a microplate, a microwell plate, a multi plate, a multi well plate, a microslide, a chamber slide, a schale, a tube, a tray, a culture bag, and a roller bottle can be used.

To promote the adhesion and spreading of cells, the inner surface of the vessel is preferably coated with any one or more selected from the group consisting of collagen, fibronectin, laminin or laminin fragments, vitronectin, basement membrane matrices, gelatin, hyaluronic acid, polylysine, vitronectin, and hyaluronic acid. Among others, laminin or laminin fragments, such as laminin E8 fragment and laminin 511E8 fragment, are preferably used.

Culture is carried out under conditions of 36° C. to 38° C., preferably 36.5° C. to 37.5° C., 1% to 25% $O_2$, and 1% to 15% $CO_2$.

The culture period is at least 1 week to 8 weeks, preferably 2 weeks to 6 weeks, more preferably 3 weeks to 5 weeks for culture in the differentiation medium for epithelium for inducing the differentiation of ocular surface epithelial stem cells.

The period is at least 1 week to 12 weeks, preferably 1 week to 8 weeks, more preferably 2 weeks to 6 weeks for culture in the medium for corneal epithelium culture for inducing the differentiation of corneal epithelial progenitor cells.

The period is at least 4 days, preferably 1 week or more, more preferably 2 to 3 weeks for stratification/maturation culture in the medium for corneal epithelium culture after isolating corneal epithelial progenitor cells.

(3) Isolation of Corneal Epithelial Progenitor Cell

The isolation of corneal epithelial progenitor cells can easily be carried out using a specific antibody for each marker according to a conventional method. For example, isolation may be carried out by separation using antibody-labeled magnetic beads, a column on which an antibody is solid-phased, or a cell sorter using a fluorescence-labeled antibody (FACS). The antibody may be a commercially available one or may be prepared according to a conventional method.

For example, the corneal epithelial progenitor cells can simply be isolated by FACS or the like using the expression of ITGβ4 and/or SSEA4 as an index. Negative selection using TRA-1-60 or CD200 is preferably carried out before positive selection using ITGβ4 or SSEA4. It has first been found that SSEA4 and CD200 can be used for the isolation of corneal epithelial progenitor cells in the present invention. SSEA4 (stage-specific embryonic antigen-4) is known to be expressed in a mesenchymal stem cell, a red blood cell, and the like in addition to teratoma, a human embryonic germ cell (EG), and a human ES cell. SSEA4 is lower in expression on a human ES cell as differentiation proceeds, and thus is widely used for evaluation by monitoring of the human ES cell differentiation. CD200 has not previously known, for example, to be expressed in a pluripotent stem cell or to be unexpressed in the corneal epithelium, and is a very excellent marker enabling the wider removal of impurities than that for known TRA-1-60.

When continued to be cultured in the medium for corneal epithelium culture, the corneal epithelial progenitor cells can differentiate into conjunctival goblet cells or lacrimal cells. The conjunctival goblet cells can be identified by the expression of MUC5AC and K7 as conjunctival goblet cell markers. The lacrimal cells can be identified by the expression of AQP5, LTF, and MUC7 as lacrimal gland/salivary gland markers, and the cells can construct glandular tissue by performing three-dimensional culture.

(4) Characteristic of Corneal Epithelial Cell

Transplantable stratified corneal epithelial cells are obtained by subjecting the corneal epithelial progenitor cells to maturation culture. The corneal epithelial cells obtained are K12-, pax6-, and p63-positive and function as corneal epithelium in vitro and in vivo like corneal epithelial cells derived from somatic cells. The present invention also provides functional corneal epithelial cells derived from pluripotent stem cells, particularly induced pluripotent stem cells, characterized by K12, pax6, and p63.

5. Use for Regenerative Medicine 5.1 Cell Medicine

The neuroectodermal lineage cells, neural crest lineage cell/optic cup lineage cells, ocular surface ectodermal lineage cells, and surface ectodermal lineage cells obtained by the method of the present invention, or the eye-related cells differentiated from the cells can be used per se for research or regenerative medicine or to prepare a cell medicine described below.

The cell medicine of the present invention may contain a scaffolding or component assisting cell maintenance/growth or administration to an affected part and a pharmaceutically acceptable carrier. Examples of the component necessary for the maintenance/growth of cells include medium components, such as carbon sources, nitrogen sources, vitamins, minerals, salts, and various cytokines, or extracellular matrix preparations, such as Matrigel™.

Examples of the scaffolding and component assisting administration to an affected part include biodegradable polymers, for example, collagen, polylactic acid, hyaluronic acid, cellulose, and their derivatives, and complexes consisting of 2 or more thereof, and aqueous solutions for injection, for example, physiological buffers, such as saline, medium, and PBS, and isotonic solutions containing glucose and other auxiliary substances (e.g., D-sorbitol, D-mannose, D-mannitol, and sodium chloride); a suitable solubilizer, for example, an alcohol, such as ethanol or polyalcohol (e.g., propylene glycol or polyethylene glycol) or a non-ionic surfactant, such as polysorbate 80 or HCO-50, may be used in combination therewith.

In addition, a pharmaceutically acceptable organic solvent, polyvinyl alcohol, polyvinylpyrrolidone, carboxyvinyl polymer, carboxymethylcellulose sodium, sodium polyacrylate, alginate sodium, water-soluble dextran, carboxymethyl starch sodium, pectin, methylcellulose, ethylcellulose, xanthan gum, gum Arabic, casein, agar, polyethylene glycol, diglycerine, glycerin, propylene glycol, vaseline, paraffin, stearyl alcohol, stearic acid, mannitol, sorbitol, or lactose, a pharmaceutically acceptable surfactant, a buffer, an emulsifier, a suspension agent, a soothing agent, a stabilizer, or the like may be contained, if necessary.

An actual additive is selected from among the above substances alone or in combination; however, it is not intended to be limited thereto.

Examples of a disease to be a target for the cell medicine of the present invention include Stevens-Johnson syndrome, ocular pemphigoid, thermal/chemical injury, aniridia, Salzmann corneal degeneration, idiopathic keratoconjunctival epithelial disorder, post-trachoma scar, corneal perforation, corneal peripheral ulcer, and corneal epithelial abrasion after excimer laser treatment.

5.2 Cultured Corneal Cell Sheet

The epithelial progenitor cell population obtained by the method of the present invention and/or the corneal epithelial cell population differentiated from the cell population can be stratified to prepare a cultured corneal epithelial cell sheet.

According to the method of the present invention, stratified sheet-like corneal epithelial cells can simply be obtained using a serum-free medium without using feeder cells. The resultant cells hold markers specific for corneal epithelial cells, such as keratin 12, pax6, and MUC16, and have the same functions as those of somatic cell-derived corneal epithelial cells. The cells are also highly safe and suited for clinical application since they are produced without using animal-derived feeder cells or serum. The present invention provides a functional stratified corneal epithelial cell sheet derived from pluripotent stem cells, particularly induced pluripotent stem cells, characterized by K12-, pax6-, and MUC16-positivity, and a method for producing the sheet.

EXAMPLES

The present invention will be described below in further detail with reference to Examples. However, the present invention is not limited to these Examples.

Example 1: Induction of Differentiation From Human iPS Cell into Ocular Surface Epithelial/Corneal Epithelial Cell From human iPS cells, ocular surface epithelial/corneal epithelial cells were differentiated in a serum-free medium without using feeder cells. The scheme of the method for differentiation induction is shown in FIG. 1.

The 201B7 cell line (an iPS cell line prepared by introducing Oct3/4, OX2, c-Myc, and Klf4 into fibroblasts) was used as human iPS cells, and the cells were seeded at a seeding density of 200 to 1,500 cells/cm$^2$, 300 to 1,000 cells/cm$^2$, or 450 to 700 cells/cm$^2$ in StemFit (from Ajinomoto Co., Inc.) on a 6-well plate coated with laminin 511E8 fragment, and cultured for 7 to 13 days.

The medium was replaced with a differentiation medium (GMEM containing 10% KSR, 1 mM sodium pyruvate, 0.1 mM non-essential amino acids, and 55 μm monothioglycerol), and then replaced with the fresh differentiation medium once every 2 to 3 days to perform culture for about 4 weeks.

The medium was replaced with a differentiation medium for epithelium containing a growth factor at or after the 4th week, and culture was further carried out for 4 weeks. At on the order of 2 to 3 weeks after replacement with a differentiation medium for epithelium (50% of a differentiation medium containing 20 ng/ml KGF, 5 ng/ml FGF2, and 10 μM Y27632, and 50% Cnt20 (or CntPR; EGF/FGF2 free (CELLnTEC)), non-epithelial cells were removed by pipetting to selectively culture only ocular surface epithelial cells in the 3rd zone. After 4 weeks of culture, the medium was replaced with a corneal epithelium culture medium, and culture was carried out for 4 weeks, followed by isolating corneal epithelial progenitor cells by FACS. The isolated corneal epithelial progenitor cells were further cultured in a corneal epithelium culture medium (DMEM/F12 (2:1) containing 20 ng/ml KGF, 10 μM Y27632, and 2% B27-supplement) for 2 to 3 weeks to prepare a stratified cultured corneal epithelial cell sheet. If necessary, after 1 to 2 weeks of culture in the corneal epithelium culture medium, it was also possible to replace the medium with a serum-containing medium for maturation culture (DMEM/F12 (3:1) containing 20 ng/ml KGF, 10 μM Y27632, insulin, transferrin, selenium, and 5% FBS), and perform culture for about 1 week to prepare the same cultured corneal epithelial cell sheet.

Figure 2:
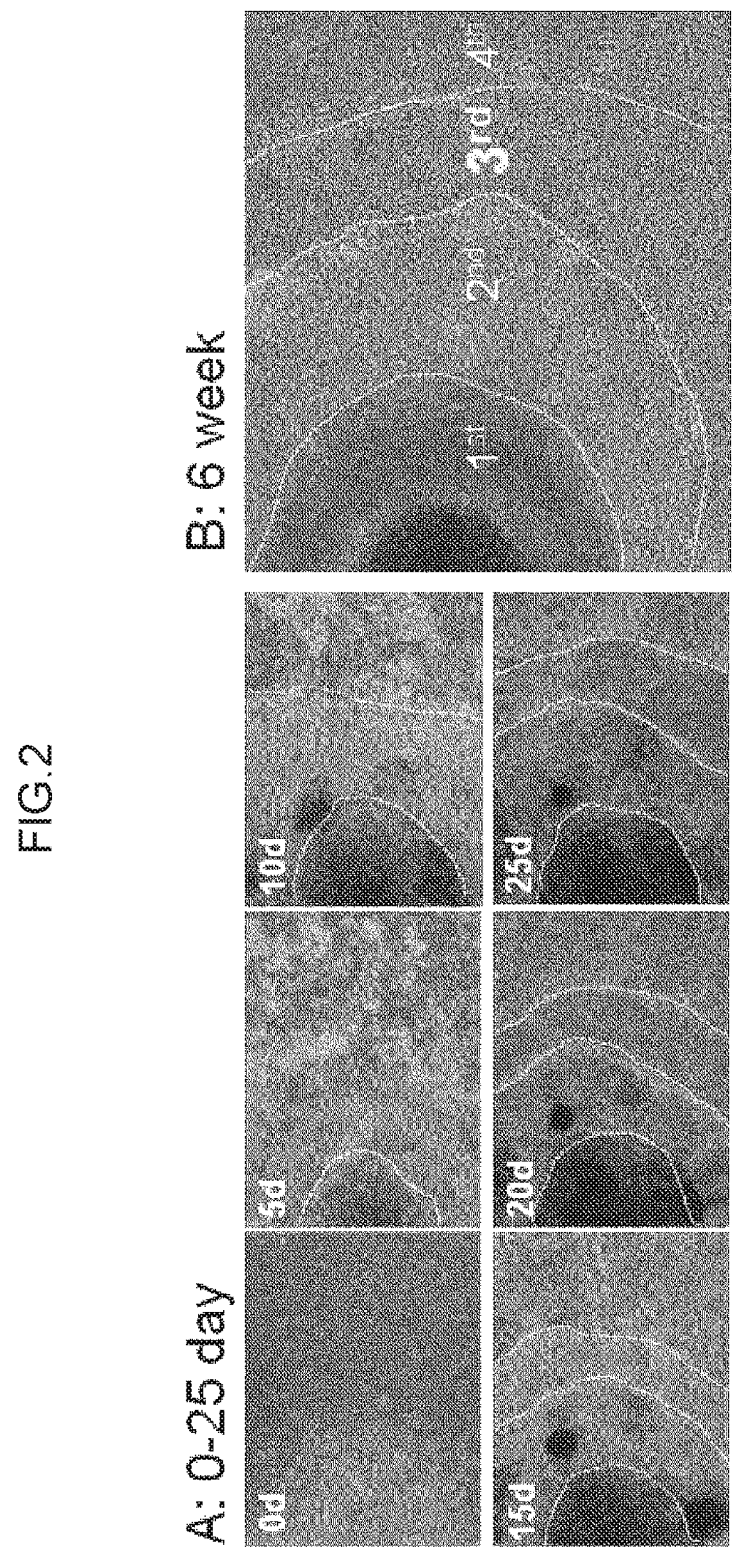

In about 4 weeks of differentiation culture, concentrically observed ectodermal lineage cells were induced to form a colony consisting of concentric zones of different ectodermal cell lineage (FIG. 2).

Figure 3:
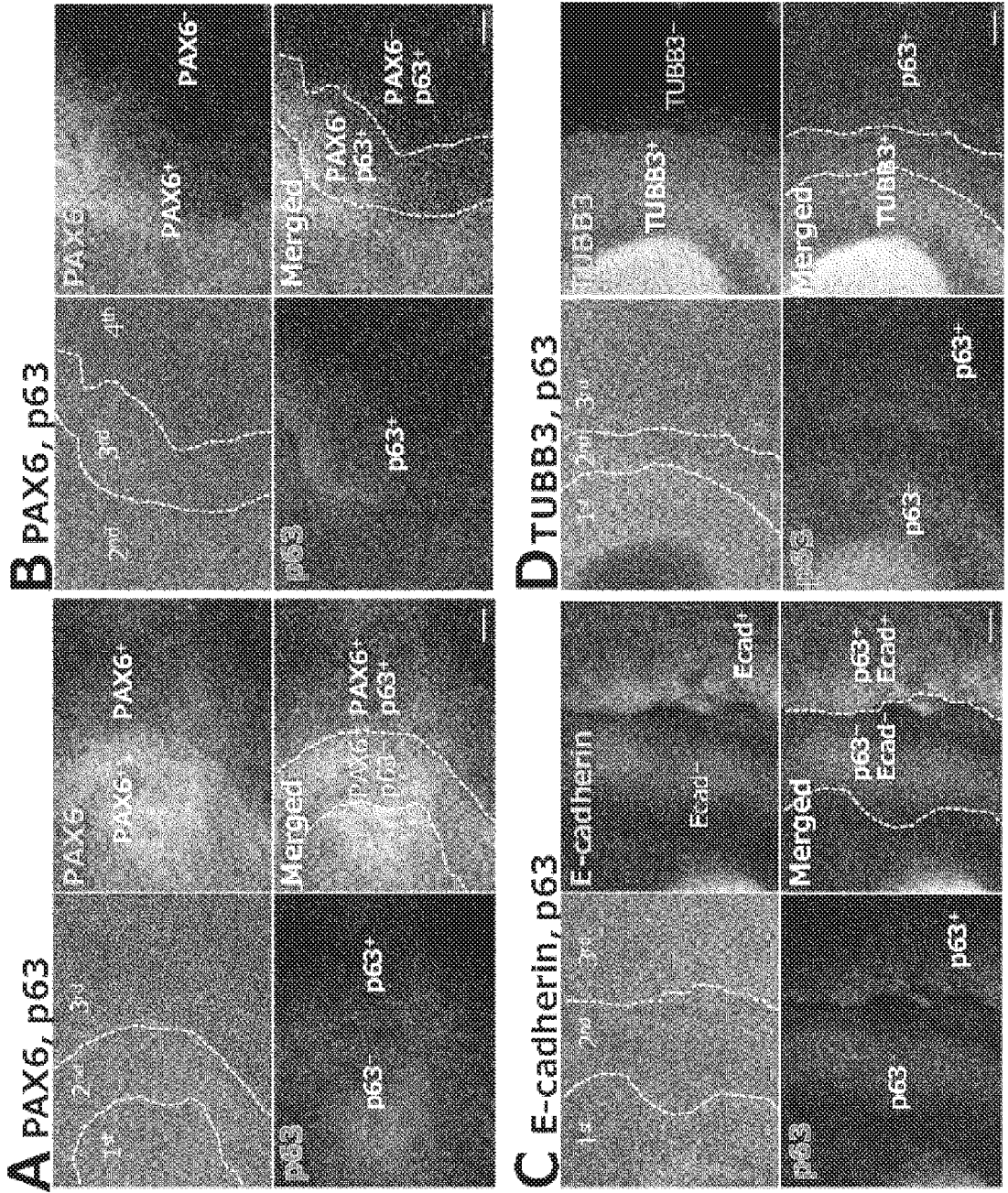

The characteristics of cells in the zones constituting the colony were examined (FIG. 3). The colony differentiated in the form of concentric zones, and cells of a different lineage were present in each zone. Specifically, the 1st to 3rd zones were pax6-positive; the 3rd to 4th zones were p63- and E-cadherin-positive; and the 1st to 2nd zones were TUBB3-positive.

Figure 4:
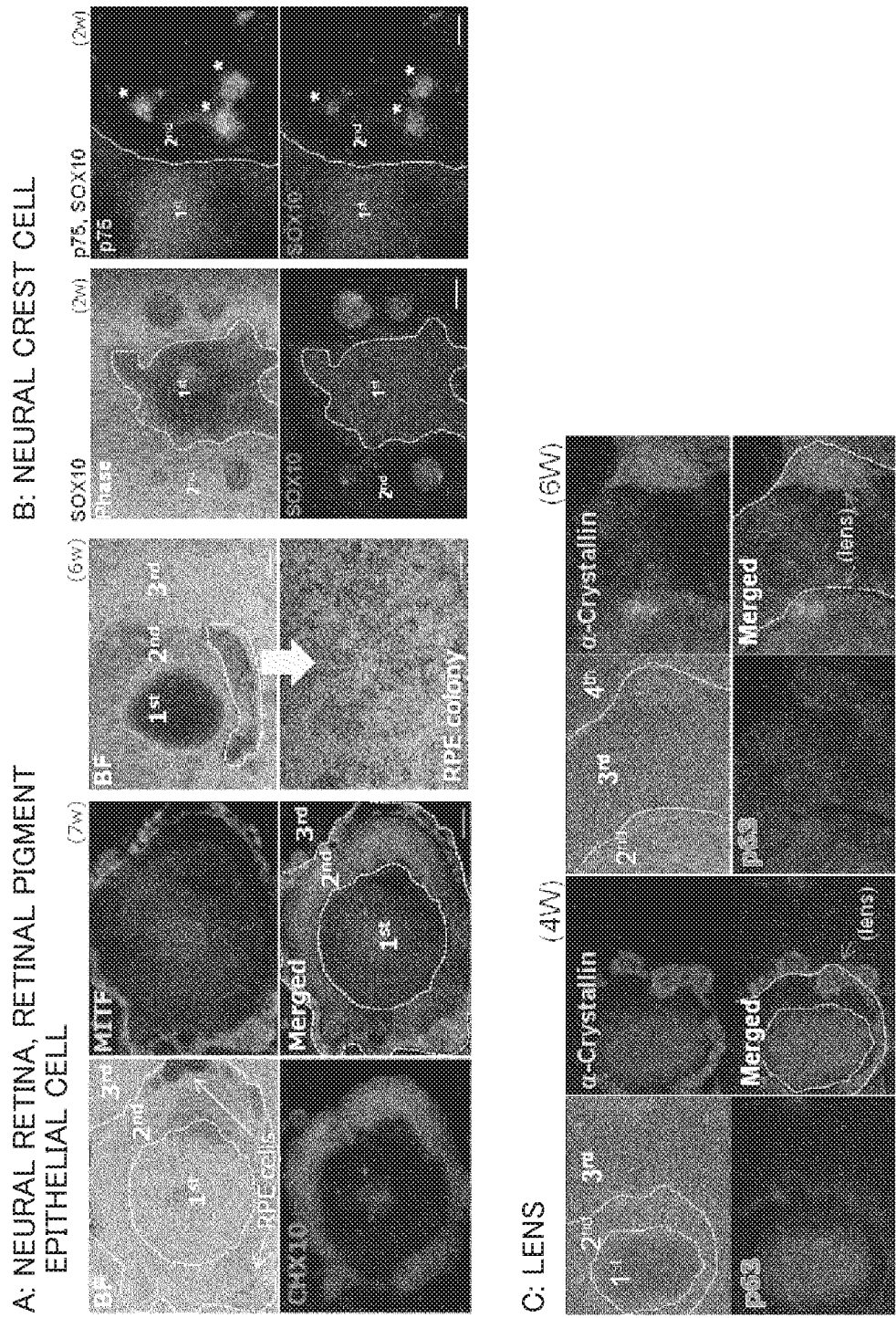
FIG. 4 is a series of photographs showing features of cells contained in zones of ectodermal cells autonomously differentiated from human iPS cells.

CHX10-positive neural retina appeared in the inner part of the 2nd zone, and MITF-positive retinal pigment epithelial cells appeared from the outer part of the zone; these cells could be isolated as pigment-containing cobblestone-like cells by picking-up and culturing the cells. Neural crest cells appeared as p75/SOX10 double positive cells in the 2nd zone portion at early differentiation (2nd week) (FIG. 4). Lens cells expressing α crystallin were confirmed to appear between the 2nd and the 3rd zones (4 weeks and 6 weeks) (FIG. 4).

Figure 5:
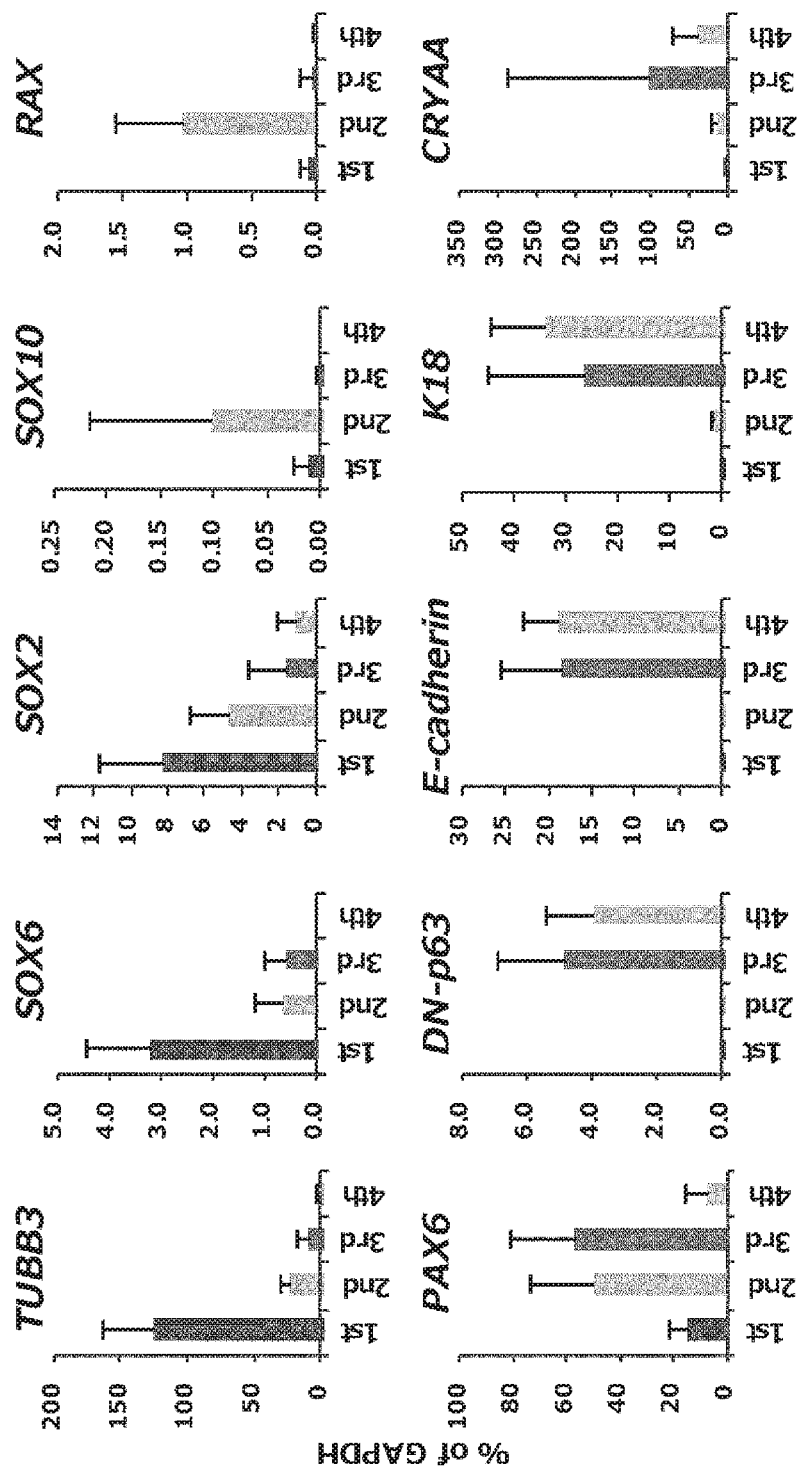
FIG. 5 is a series of graphs showing the expression of markers in zones of ectodermal cells autonomously differentiated from human iPS cells (the first zone (1st): neuroectodermal lineage (Sox2+, TUBB3+, and Sox6+), the 2nd zone (2nd): neural crest/optic vesicle cell lineage (pax6+, Sox10+, and Rx+), the 3rd zone (3rd): ocular surface ectodermal lineage (pax6+, p63+, E-cadherin+, and K18), and the 4th zone (4th): surface ectodermal lineage (p63+, E-cadherin+, and K18+).

The marker expression in each zone was examined by RT-PCR (FIG. 5). Ocular surface epithelial ectoderm (pax6+, p63+, and Ecad+) representing the origin of the corneal epithelium appeared from the 3rd zone.

Figure 6:
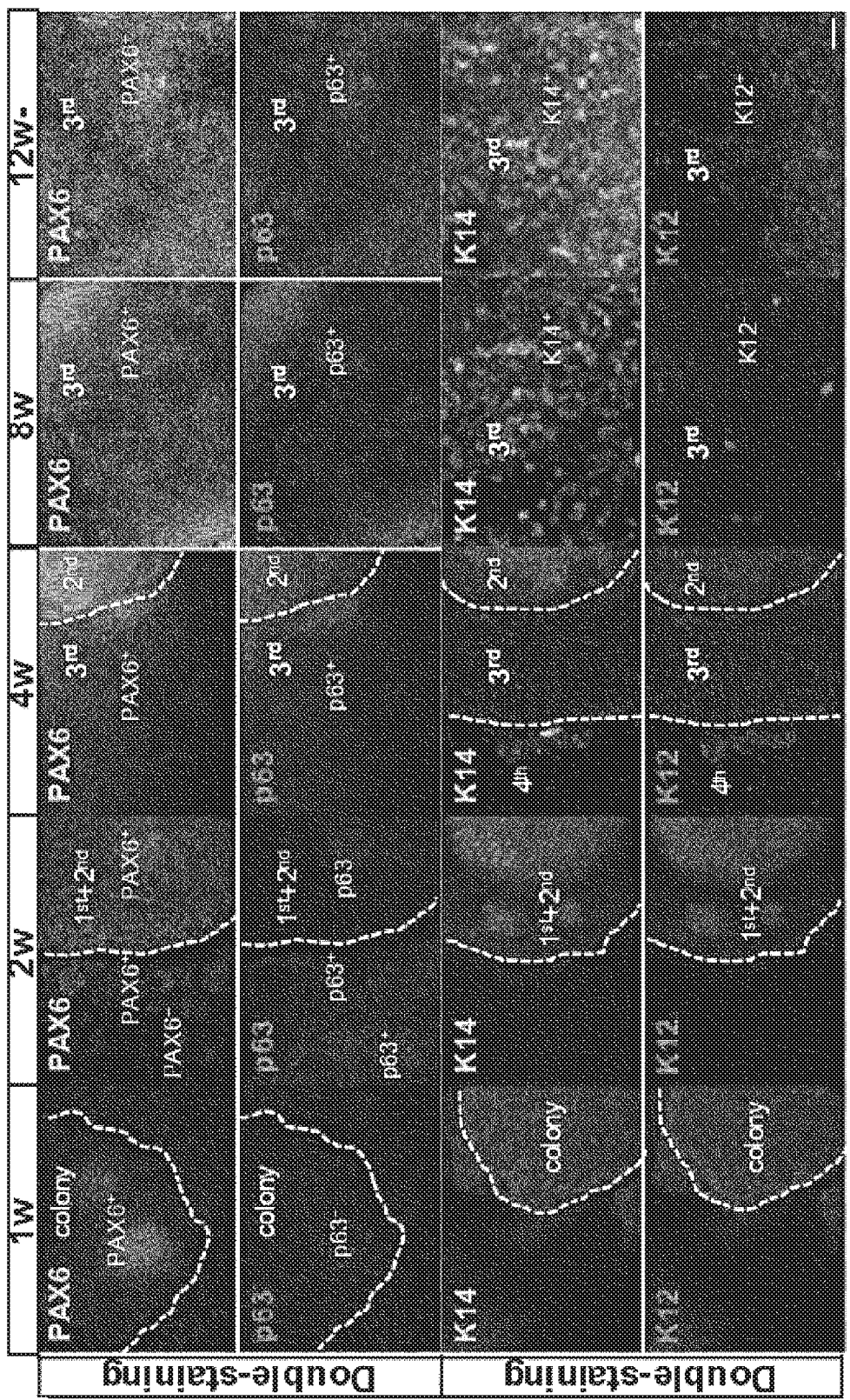
FIG. 6 is a series of photographs showing the expression of corneal epithelium-related markers during the period of differentiation induction (1 to 12 weeks).
Figure 7:
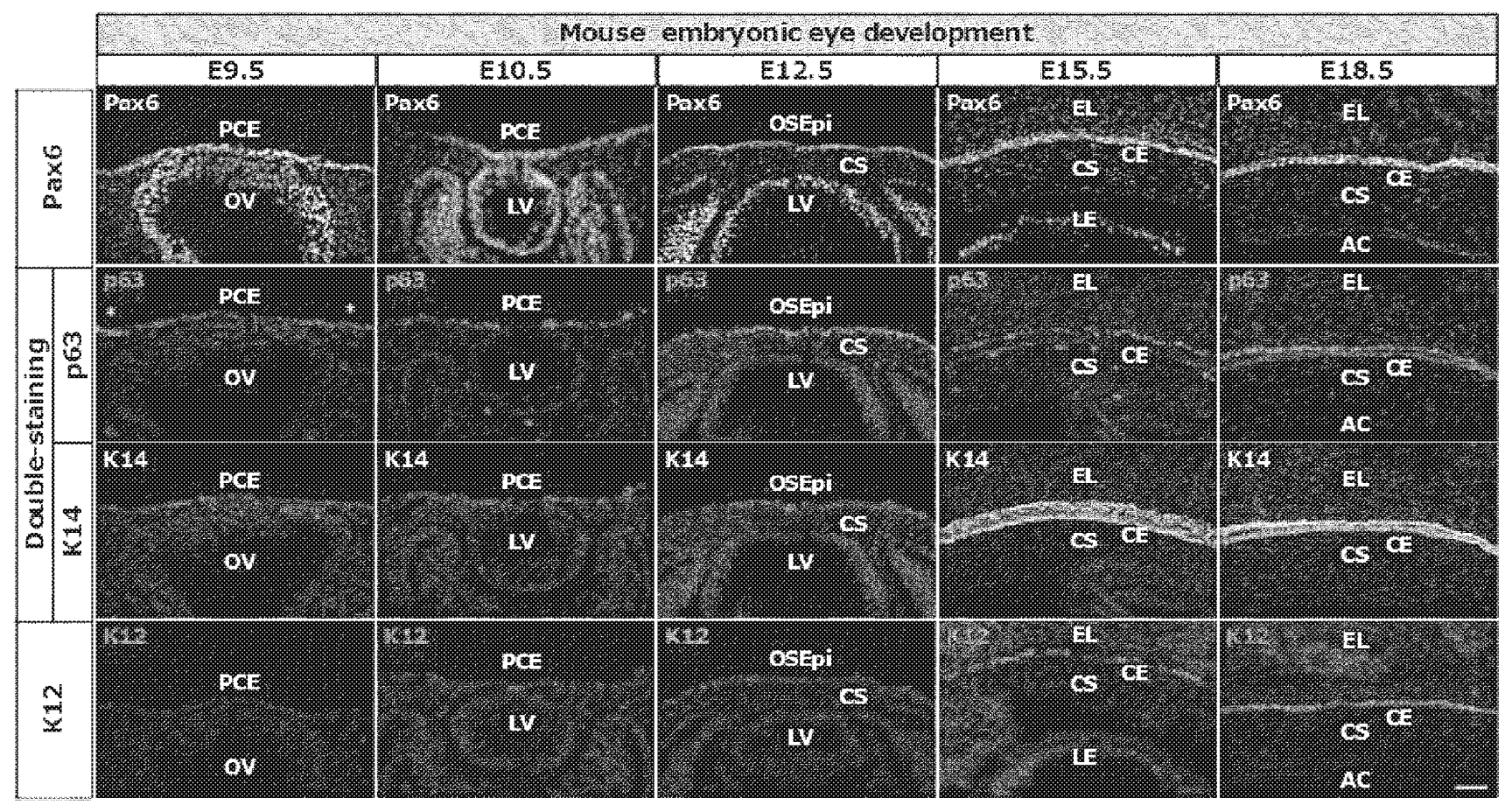

In addition, the identification of the expression pattern (at 1 to 12 weeks of differentiation) of corneal epithelium-related markers (K12, K14, p63, and pax6) during the period of differentiation induction by immunostaining (FIG. 6) confirmed that the pattern was quite similar to that of the corneal epithelium-related marker expression in mouse eye development (E9.5 to 18.5) (FIG. 7) and the induction of the ocular surface epithelium/corneal epithelium from iPS cells occurred through the same process as the actual corneal developmental process.

The above results confirmed that the present culture method could be used to induce an eye-related cell population, including ocular surface epithelial cells, (retina, lens, neural crest cells, etc.) from human pluripotent stem cells in the form of mimicking a physiological development of the cells.

Example 2: Induction of Differentiation of Corneal Epithelial Progenitor Cell From Human iPS Cell The colonies having the form of concentric circles, formed by the autonomous differentiation (4 weeks) of human iPS cells according to Example 1 were each isolated by replacing the medium with a differentiation medium for epithelium containing a growth factor at or after the 4th week and removing non-epithelial cells by pipetting from ocular surface epithelial stem cells appearing in the 3rd zone. In addition, at or after the 8th week, the medium was replaced with a corneal epithelium culture medium, and differentiation into corneal epithelial progenitor cells was induced.

Figure 8:
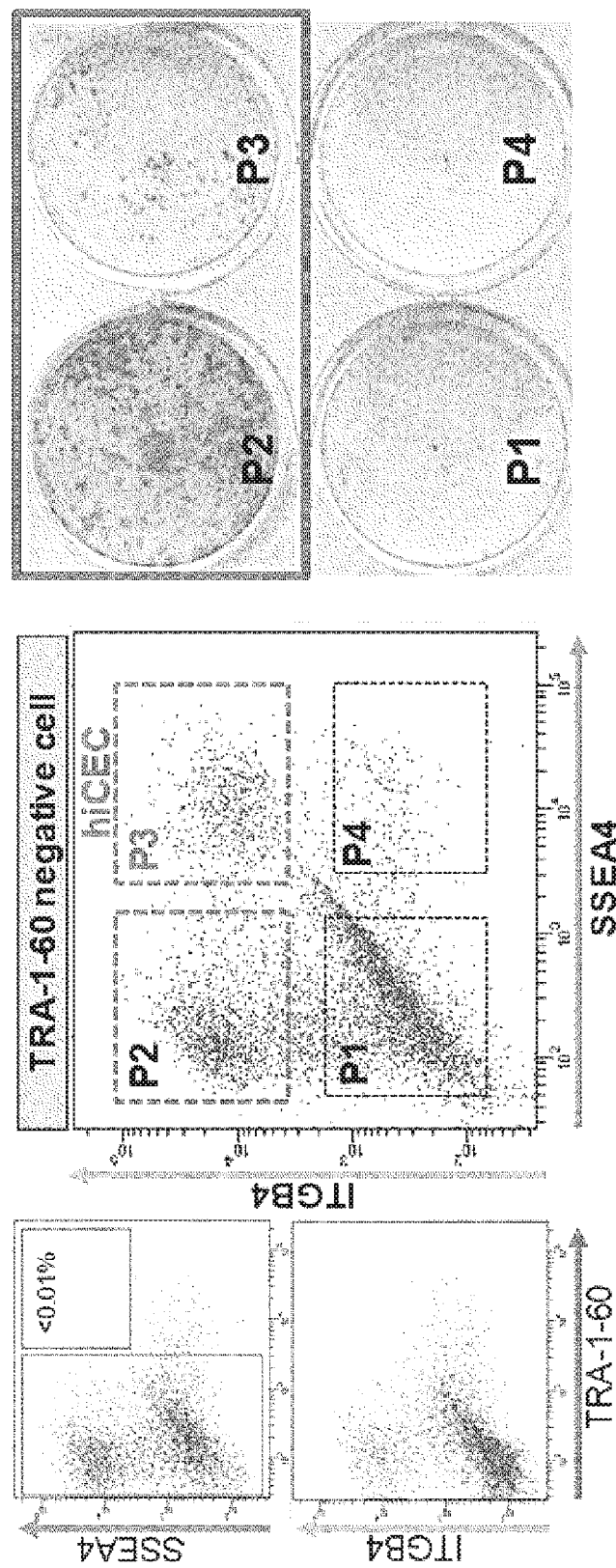
FIG. 8 illustrates the isolation of corneal epithelial progenitor cells by FACS at the 12th week of differentiation culture of 3rd-zone cells (P1: the 1st zone, P2: the 2nd zone, P3: the 3rd zone, and P4: the 4th zone).

At about the 12th week of differentiation induction, FACS was carried out using cell surface markers, such as TRA-1-60, SSEA4 and ITGB4 (FIG. 8). It was identified that the corneal epithelial progenitor cells could be isolated based on the expression of TRA-1-60, SSEA4, and ITGB4 and were selectively present in ITGB4-positive and SSEA4-positive cells (P3) and ITGB4-positive and SSEA4-negative cells (P2) among TRA-1-60-negative cells (FIG. 8 right).

Figure 9:
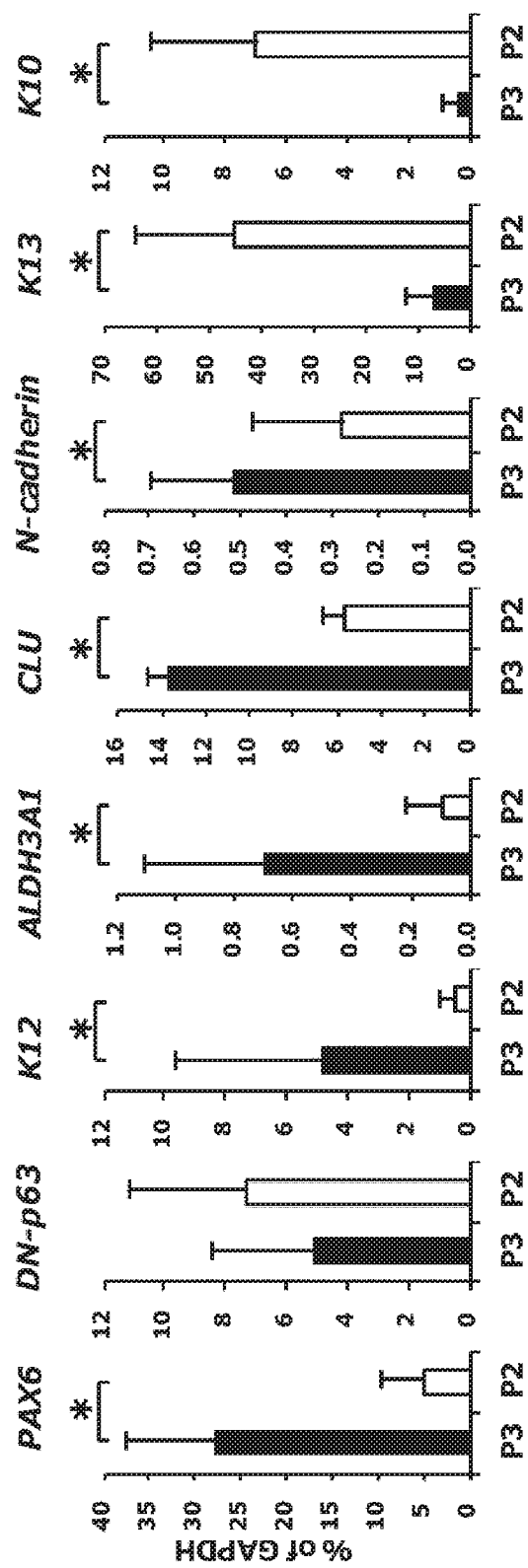
FIG. 9 is a series of graphs showing the expression of corneal epithelial markers in the 2nd zone (P2) and the 3rd zone (P3).
Figure 10:
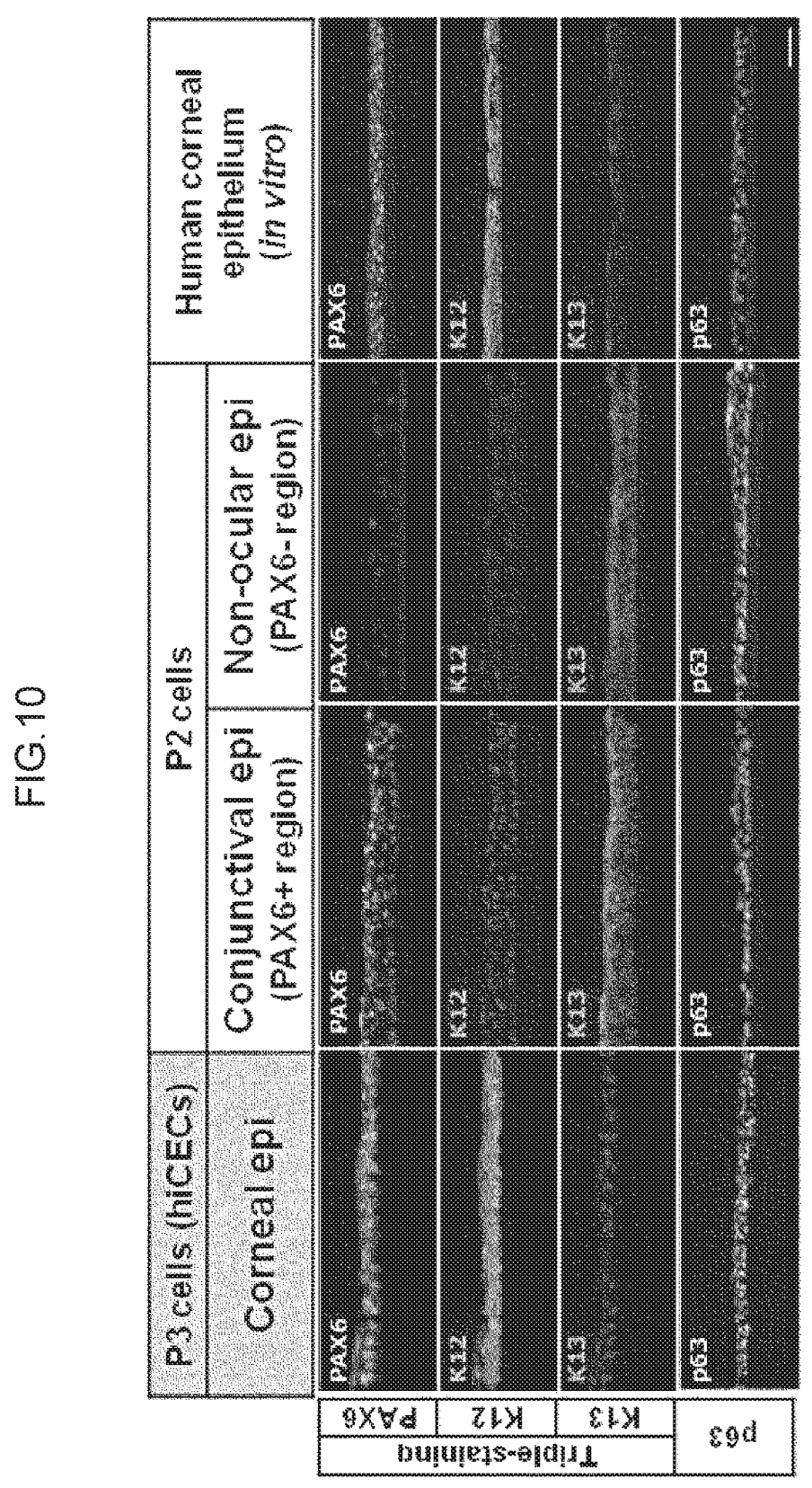

In addition, the results of immunostaining showed that cells in the P3 zone expressed corneal epithelium-specific markers while being low in the expression of mucosal epithelium and cutaneous epithelium markers (FIG. 9). This demonstrated that corneal epithelial cells were isolated in the P3 zone and conjunctival epithelium and other stratified epithelial cells were contained in the P2 zone (FIG. 10).

Figure 11:
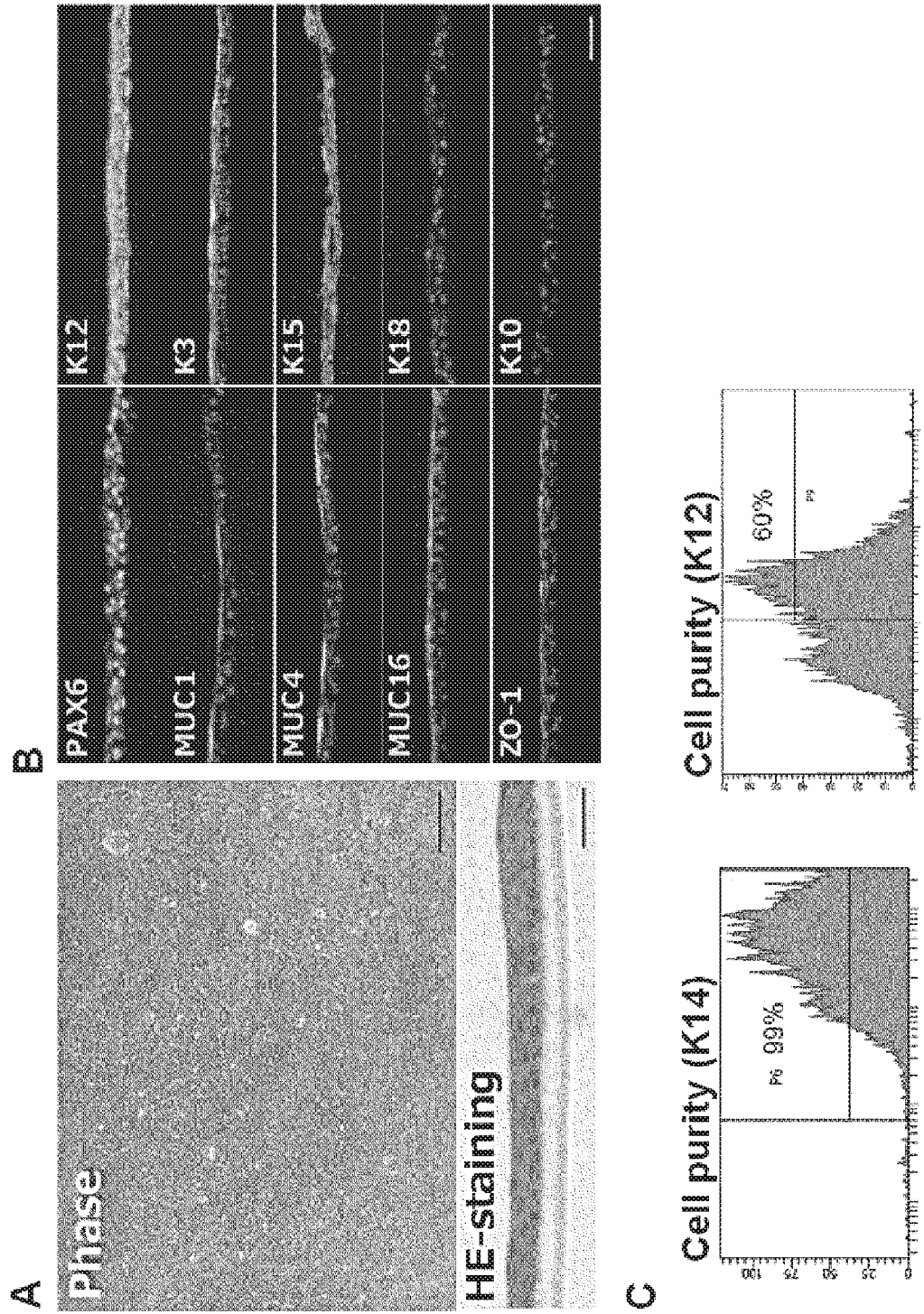
FIG. 11 illustrate marker expression after maturation culture of corneal epithelial cells (derived from the 3rd zone (P3)) differentiated from human iPS cells.

The cells isolated from the P3 zone were subjected to maturation culture for 2 to 3 weeks using a corneal epithelium culture medium to provide stratified corneal epithelial cells. The results of immunostaining showed that the resultant cells expressed markers essential for corneal barrier function, ZO-1, MUC1, MUC4, and MUC16 (FIG. 11B). As a result of FACS analysis, the purity of K14-positive cells was about 99%, and the positive rate of the corneal epithelial differentiation marker K12 was about 60% (FIG. 11C).

Example 3: Transplantation of Human iPS Cell-Derived Corneal Epithelial Cell Sheet onto Rabbit Eye The epithelial cell layer on the whole circumference of the rabbit corneal limbus was removed by corneal abscission to prepare a rabbit corneal epithelial stem cell deficiency model. Then, a human iPS cell-derived corneal epithelial cell sheet recovered in sheet form was transplanted.

(1) Ocular Surface Observation Image

At the 7th day after transplantation, corneal transparency was kept in a sheet transplantation group, and fluorescein staining showed that barrier function had been recovered. On the other hand, a large part of the control eye was stained by fluorescein and remained in a state of barrier dysfunction (FIG. 12 middle).

(2) Human iPS Cell-Derived Corneal Epithelial Cell Sheet After Transplantation

Each rabbit was euthanized on postoperative day 7, and the eyeball was excised and then chemically fixed with a 10% neutral buffered formalin solution. Then, corneal tissue was observed by hematoxylin-eosin staining. The human iPS cell-derived corneal epithelial cell sheet was also engrafted on the surface of the corneal stroma after transplantation onto the animal eye.

Figure 12:
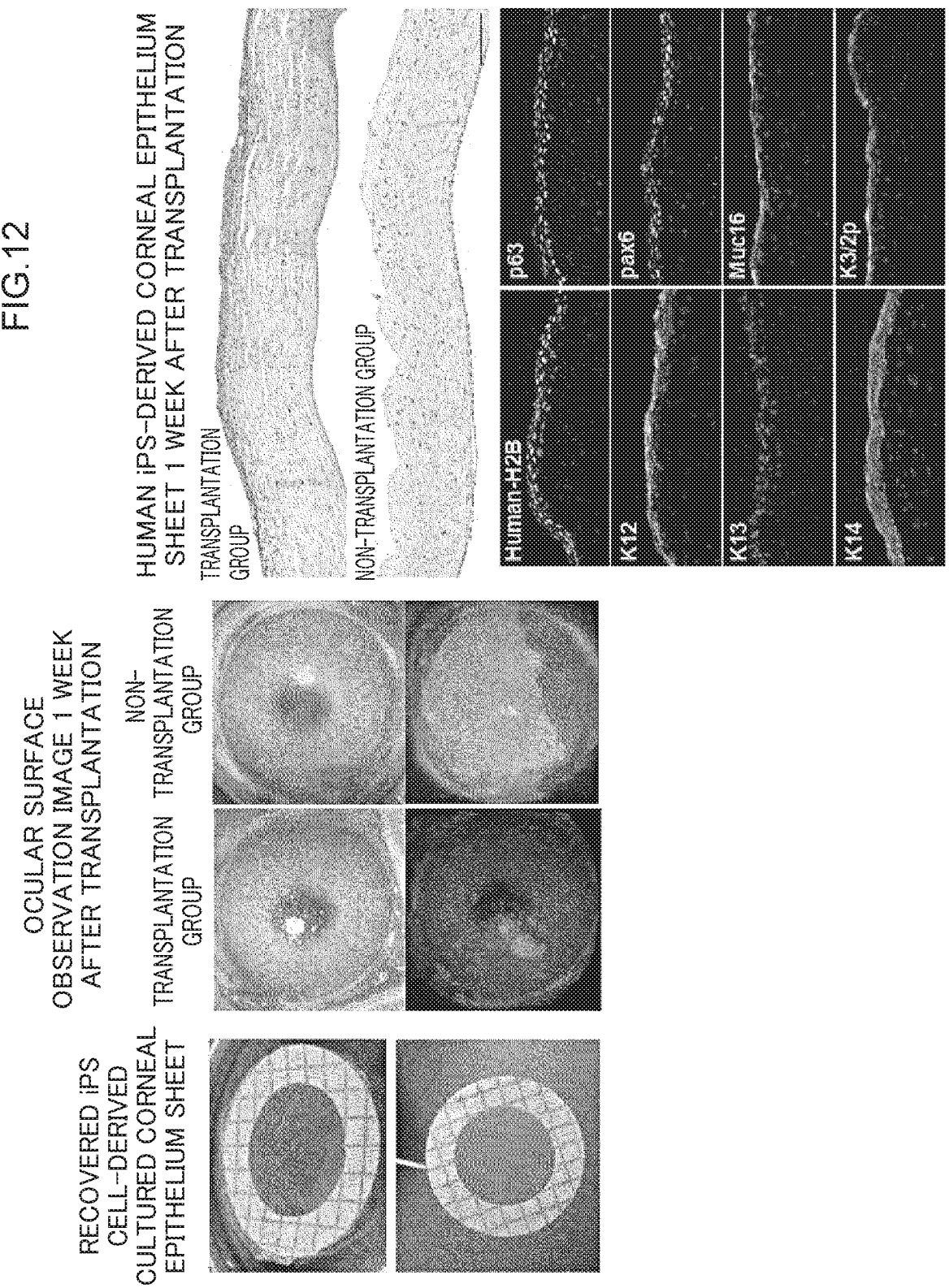
FIG. 12 is a series of photographs showing the results of transplanting a human iPS cell-derived corneal epithelial cell sheet onto a rabbit eye. The human iPS cell-derived corneal epithelial cell sheet can be recovered in sheet form (left). During slit observation after transplantation, fluorescein staining (upper right) and immunohistochemical analysis (lower right) show that the human iPS cell-derived corneal epithelial cell sheet is engrafted on the surface of the corneal stroma after transplantation and exhibits corneal barrier function.

Immunostaining analysis with an anti-human (H2B) antibody using frozen sections demonstrated that the epithelial layer engrafted on the rabbit eye is derived from human iPS cells and could identify that the layer expressed K12, pax6, p63, and MUC16 and held the properties of the corneal epithelium (FIG. 12 right).

Example 4: Induction of Differentiation of Conjunctival Goblet Cell-Like Cell and Lacrimal Gland-Like Cell From Human iPS Cell The colonies having the form of concentric circles, formed by the autonomous differentiation (4 weeks) of human iPS cells according to Example 1 were each isolated by replacing the medium with a differentiation medium for epithelium containing a growth factor at or after the 4th week and removing non-epithelial cells by pipetting from ocular surface epithelial stem cells appearing in the 3rd zone. In addition, at or after the 8th week, the medium was replaced with a corneal epithelium culture medium, and differentiation into corneal epithelial progenitor cells was induced.

After inducing differentiation into corneal epithelial progenitor cells, culture was further continued in the corneal epithelium culture medium while replacing the medium every 2 to 3 days. At about the 12th week from inducing differentiation, a PAS-positive and PAX6-positive cell population appeared among an epithelium-like cell population in the corneal epithelium culture medium. The results of PAS staining and immunostaining demonstrated that these cells expressed MUC5AC and K7 as conjunctival goblet cell markers (FIG. 13A).

Similarly, after differentiation into corneal epithelial cells, culture was continued in the corneal epithelium culture medium while replacing the medium. At about the 12th week from the differentiation induction, a cell aggregate having a gland-like structure appeared in the corneal epithelium culture medium. The gland-like tissue was collected under a microscope and subjected to 3-dimensional culture in Matrigel® using a KCM medium containing 5% FBS, EGF, and Wnt3awp or a DMEM/F12 medium containing 2% B27; as a result, the tissue developed into gland tissue in about 25 days. Immunostaining demonstrated that the gland tissue expressed AQP5, LTF, MUC7, PAX6, and SOX9 as the lacrimal gland/salivary gland markers (FIG. 13B).

The above results demonstrated that the ocular surface epithelial stem cells/progenitor cells induced from human pluripotent stem cells could be differentiated into not only corneal epithelium but also conjunctival epithelial cells, conjunctival goblet cells, and lacrimal cells considered to have the same developmental origin as the corneal epithelium Example 5: Induction of Differentiation of Periocular Neural Crest Cell From Human iPS Cell Human iPS cells were autonomously differentiated in a differentiation medium (for 4 weeks) according to Example 1 to induce differentiation into colonies each having the form of concentric circles (multi-zone structures). At the 3rd week from the differentiation induction, a PITX2-positive and AP2b-positive cell mass (periocular neural crest cells) was induced mainly in the 2nd zone.

The cell mass could be induced when culture was carried out in a medium in which EGF, FGF2 (1 to 3 weeks), and low concentration (0.5 µM) retinoic acid (2 to 3 weeks) were added to the differentiation medium.

The marker gene expression was identified by RT-PCR at the 9th day, the 14th day, the 21st day, the 28th day, and the 35th day from the start of differentiation culture. As a result, it was demonstrated that after an early neural crest marker, SOX10, disappeared in 4 weeks, the expression of periocular neural crest markers, such as PITX2 and FOXC1, was induced. Thus, human iPS cell-derived early neural crest cells were shown to be induced into periocular neural crest cells.

The above results showed that periocular neural crest cells providing the developmental origin of neural crest cells as well as corneal endothelial and iris stromal cells could be induced using the colonies each consisting of concentric zones of ectodermal cell lineage induced by the present invention. It is probable that the addition of EGF, FGF, and low concentration (0.5 µM) retinoic acid to the differentiation medium promoted the growth of retinal cells in the 2nd zone and the addition of the retinoic acid signal promoted the induction of periocular neural crest cells. The retinoic acid signal derived from retinal cells is considered to be important for the development of the periocular neural crest, and the use of this culture system probably resulted in mimicking its development.

Example 6: Isolation of Corneal Epithelial Progenitor Cell Induced From Human iPS Cell Human iPS cells were autonomously differentiated in a differentiation medium according to Example 1 to induce differentiation into colonies each having the form of concentric circles (multi-zone structures). At the 14th week from the differentiation induction, FACS was carried out using CD200, SSEA4, and ITGβ4 as cell surface markers.

Figure 15:
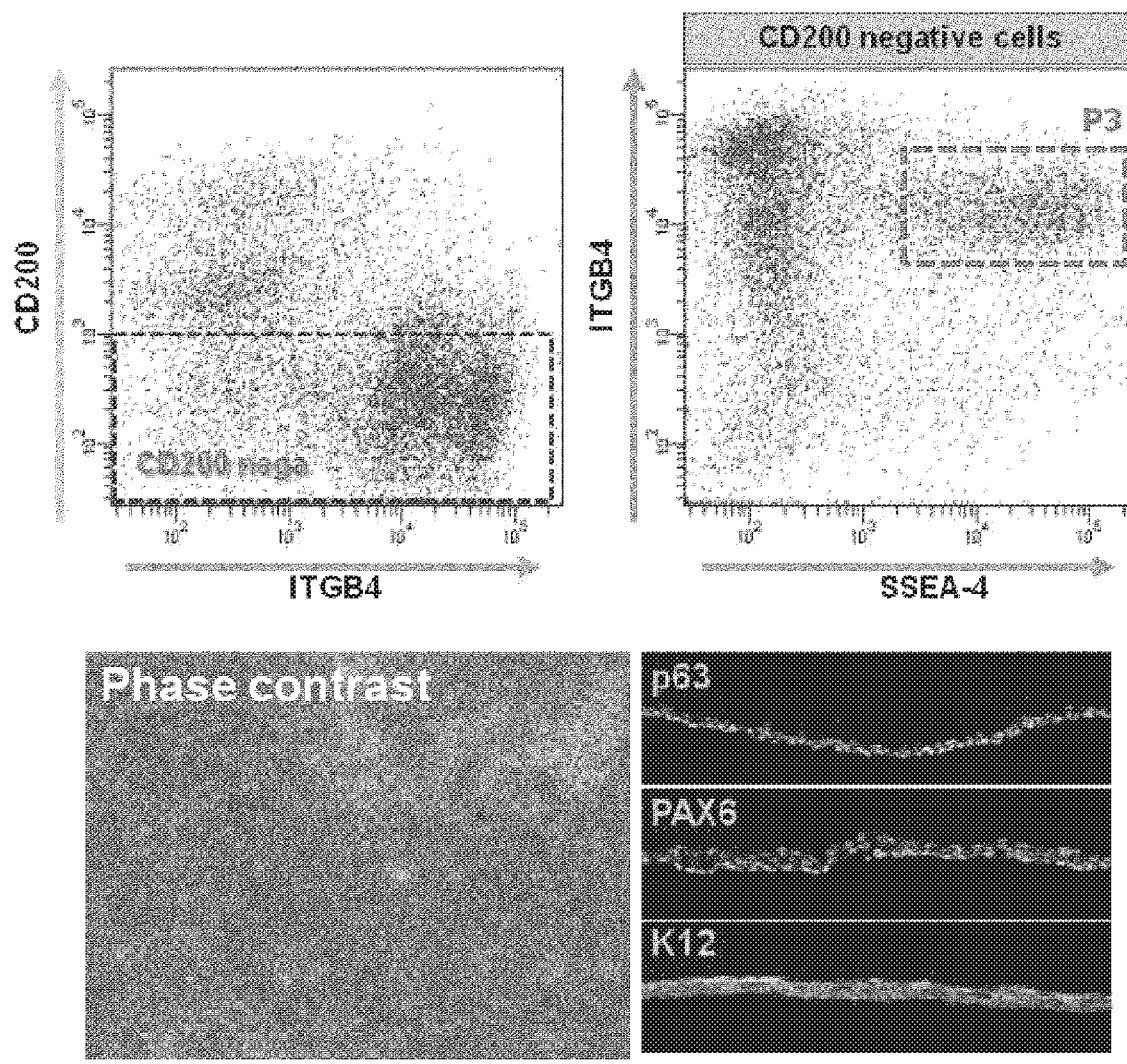
FIG. 15 illustrates is isolation using a negative marker (CD200) for corneal epithelial progenitor cells induced from iPS cells. Among CD200-negative cells, cells isolated as SSEA4-positive and ITGβ4-positive cells (P3) were stratified, expressed K12, p63, and PAX6, and showed features of differentiated corneal epithelial cells.

CD200-positive cells could be removed by gating to isolate SSEA4-positive and ITGβ4-positive cells (P3) as corneal epithelial progenitor cells from among CD200-negative cells. The isolated cells were stratified, expressed K12, p63, and PAX6, and showed features of differentiated corneal epithelial cells (FIG. 15).

The above results demonstrated that the corneal epithelial progenitor cells induced from iPS cells could be purified using CD200, SSEA4, and ITGβ4. CD200 heretofore has not been known, for example, to be expressed in pluripotent stem cells and to be not expressed in the corneal epithelium, and is probably a very excellent marker enabling the wider removal of impurities than that for known TRA-1-60.

INDUSTRIAL APPLICABILITY

According to the present invention, transplantable, stratified, functional, and highly pure corneal epithelial cells are obtained. The method of the present invention does not use animal-derived feeder cells or serum and thus the cells obtained are highly safe and suited for clinical application. In addition, according to the method of the present invention, various cells constituting not only corneal epithelium but also the ocular surface, such as conjunctival epithelium, can be prepared from pluripotent stem cells, such as human iPS cells.

All publications, patents, and patent applications cited herein are intended to be incorporated herein by reference in their entirety.

The invention claimed is:

1. A colony consisting of concentric circular-like zones of different ectodermal cell lineages derived from induced pluripotent stem cells, wherein the concentric zones comprise a first zone consisting of neuroectodermal lineage cells, a second zone consisting of neural crest lineage cells and optic cup lineage cells, a third zone consisting of ocular surface ectodermal lineage cells, and a fourth zone consisting of surface ectodermal lineage cells.

2. The colony according to claim 1, wherein the pluripotent stem cells are human induced pluripotent stem cells.

\* \* \* \* \*